US006800468B1

(12) United States Patent
Clausen et al.

(10) Patent No.: US 6,800,468 B1
(45) Date of Patent: Oct. 5, 2004

(54) UDP-GALACTOSE: β-N-ACETYL-GLUCOSAMINE β1, 3GALACTOSYLTRANSFERASES, β3GAL-T5

(76) Inventors: Henrik Clausen, Norske Allé 3, Holte (DK), DK-2840; Margarida Amado, 3137-L Via Alicante, La Jolla, CA (US) 92037

( * ) Notice: Subject to any disclaimer, the term of this patent is extended or adjusted under 35 U.S.C. 154(b) by 0 days.

(21) Appl. No.: 09/831,630

(22) PCT Filed: Nov. 11, 1999

(86) PCT No.: PCT/US99/26807

§ 371 (c)(1),
(2), (4) Date: May 10, 2001

(87) PCT Pub. No.: WO00/29558

PCT Pub. Date: May 25, 2000

(30) Foreign Application Priority Data

Nov. 13, 1998 (DK) .................................... 1998 01483

(51) Int. Cl.$^7$ ........................... C12N 15/09; C12N 9/00; C12N 9/10; C12N 1/20; C12N 15/00; C07H 21/04; C07K 1/00

(52) U.S. Cl. ....................... 435/193; 435/69.1; 435/183; 435/252.3; 435/320.1; 435/333; 435/348; 435/349; 435/354; 435/358; 536/23.2; 536/23.4; 536/23.5; 536/24.31; 536/24.33; 530/350

(58) Field of Search .................. 435/69.1, 183, 435/193, 252.3, 348, 349, 353, 354, 358; 320.1; 536/23.2, 23.4, 23.5, 24.31, 24.33; 530/350

(56) References Cited

U.S. PATENT DOCUMENTS

| | | | |
|---|---|---|---|
| 4,857,639 A | 8/1989 | Clausen et al. |
| 4,942,224 A | 7/1990 | Clausen et al. |
| 5,059,520 A | 10/1991 | Furukawa et al. |
| 5,068,191 A | 11/1991 | Clausen et al. |
| 5,229,289 A | 7/1993 | Kjeldsen et al. |
| 5,240,833 A | 8/1993 | Nudelman et al. |
| 5,326,857 A | 7/1994 | Yamamoto et al. |
| 5,418,129 A | 5/1995 | Nudelman et al. |
| 5,421,733 A | 6/1995 | Nudelman et al. |
| 5,660,834 A | 8/1997 | Kjeldsen et al. |
| 5,747,048 A | 5/1998 | Kjeldsen et al. |
| 5,871,990 A | 2/1999 | Clausen et al. |

FOREIGN PATENT DOCUMENTS

| | | |
|---|---|---|
| EP | 0 395 217 A2 | 10/1990 |
| JP | 06181759 | * 7/1994 |
| WO | WO 91/11199 | 8/1991 |
| WO | WO 91/11528 | 8/1991 |
| WO | WO 97/43405 | 11/1997 |

OTHER PUBLICATIONS

Amado, et al., 1998, J. Biol Chem, 273:12770–12778.
Bax et al., 1985a, J. Magn. Reson., 65:355–360.
Bax et al., 1985b, J. Magn. Reson., 63:207–213.
Bodenhausen et al., 1980, Chem. Phys. Lett., 69:185–189.
Bothner et al., 1984, J. Am. Chem. Soc., 106:811–813.
Braunschweiler et al., 1983, J. Magn. Reson., 53:521–528.
Breton et al., 1998, J. Biochem., 123:1000–1009.
Clausen et al., 1989, Vox Sanguinis, 56:1–20.
Clausen et al., 1990, J. Biol. Chem. 265:1139–1145.
Dabrowski et al., 1980, Biochemistry 19:5652–5658.
Davis et al., 1992, J. Magn. Reson., 98:207–216.
Hakomori et al., 1989, Advances in Cancer Research, 52:257–331.
Hakomori et al., 1996, Cancer Res. 56:5309–5318.
Hennett et al., 1998, J. Biol Chem. 273:58–65.
Holmes et al., 1989, Arch Biochem Biophys. 270:630–646.
Kannagi et al., 1983, J. Biol. Chem. 258:8934–8942.
Kobata et al., 1992, Eur. J. Biochem. 209:483–501.
Kolbinger et al., 1998, J. Biol. Chem. 273:433–440.
Kozak et al., 1992, Ann Rev. Cell Biol, 8:197–225.
Kyte et al., 1982, Journal of Molecular Biology 157:105–132.
Martensson et al., 1998, Eur. J. Biochem.
Miyazaki et al., 1997, J. Biol. Chem. 272:24794–24799.
Oriol et al., 1986, Vox Sanguinis, 51:161–171.
Seko et al., 1996, Cancer Res. 56::3468–3473.
Sheares et al., 1983, J. Biol. Chem. 258:9893–9898.
Sheares et al., 1982, J. Biol. Chem. 257:599–602.
Sutherlin et al., 1997, Cancer Res. 57:4744–4748.

(List continued on next page.)

Primary Examiner—Manjunath Rao
(74) Attorney, Agent, or Firm—Morgan, Lewis & Bockius, LLP

(57) ABSTRACT

A novel gene defining a novel enzyme in the UDP-D-galactose: β-N-acetylglucosamine/β-N-acetylgalactosamine β1,3galactosyltransferase family, termed β3Gal-T5, with unique enzymatic properties is disclosed. The enzymatic activity of β3Gal-T5 is shown to be distinct from that of previously identified enzymes of this gene family. The invention discloses isolated DNA molecules and DNA constructs encoding β3Gal-T5 and derivatives thereof by way of amino acid deletion, substitution or insertion exhibiting β3Gal-T5 activity, as well as cloning and expression vectors including such DNA, cells tranfected with the vectors, and recombinant methods for providing β3Gal-T5. The enzyme β3Gal-T5 and β3Gal-T5-active derivatives thereof are disclosed, in particular soluble derivatives comprising the catalytically active domain of β3Gal-T5. Further, the invention discloses methods of obtaining β1,3galactosyl glycosylated saccharides, glycopeptides or glycoproteins by use of an enzymically active β3Gal-T5 protein or fusion protein thereof or by using cells stably transfected with a vector including DNA encoding an enzymatically active β3Gal-T5 protein as an expression system for recombinant production of such glycopeptides or glycoproteins. Also a method for the identification of DNA sequence variations in the β3Gal-T5 gene by isolating DNA from a patient, amplifying β3Gal-T5-coding exons by PCR, and detecting the presence of DNA sequence variation, are disclosed.

29 Claims, 5 Drawing Sheets

OTHER PUBLICATIONS

Figure 3:
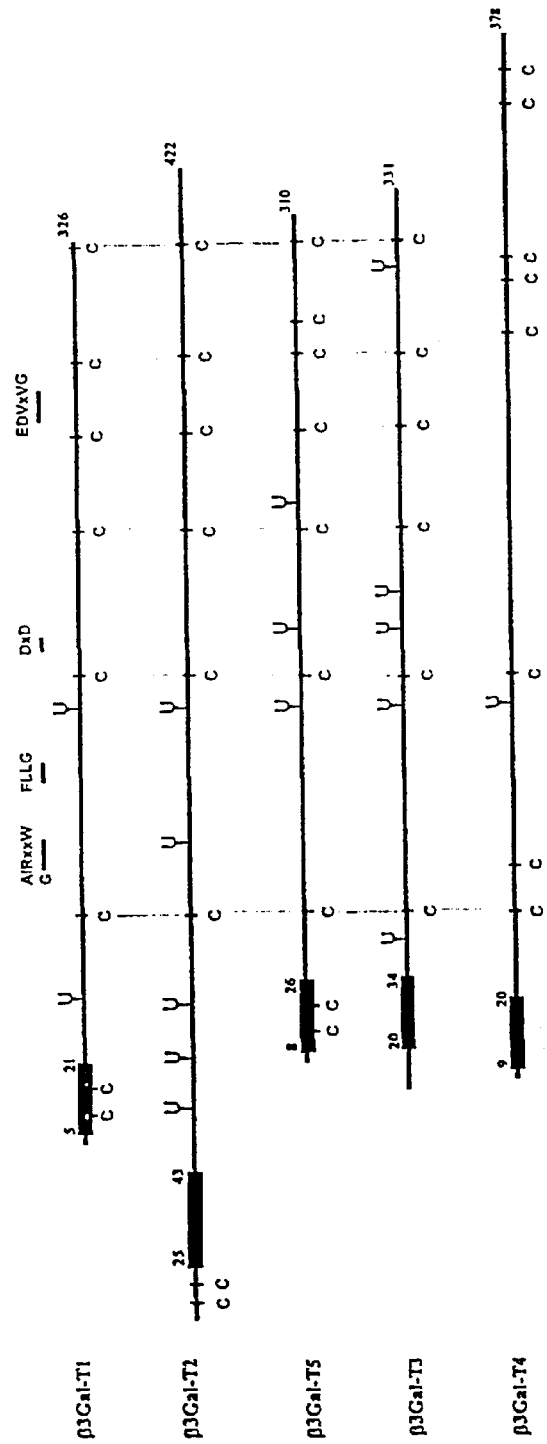

Van Halbeek et al., 1982, Eur. J. Biochem 7–20.

Wandall et al., 1997, J. Biol. Chem. 272:23503–23514.

Wiggins et al., 1998, Natl. Acad. Sci USA 95:7945–7950.

Almeida, et al., 1997, Journal of Biological Chemistry 272:31979–31991.

Pollex–Kruger, et al., 1993, Glycoconjugate Journal 10:365–380.

Schwientek, et al., 1998, Journal of Biological Chemistry 273:29331–29340.

Almeida, R., Amado, M., David, L., et al. A Family of Human 4–Galactosyltransferases: Cloning and expression of two novel UDP–GalactOSe –N–Acetylglucosaflhine 1,4–Galactosyltransferases, 4Gal–T2 and 4Gal–T3. *J. Biol. Chem.* 272:31979–31992, 1997.

Amado, M., Almeida, R., Carneiro, F., et al. A family of human 3–galactosyltransferases: characterisation of four members of a UDP–galactose –N–acetylglucoSamine/ –N–acetylgalactosamine 1,3galactosyltransferase family. *J. Biol. Chem.* 273:12770–12778, 1998.

Bennett, E.P., Hassan, H. and Clausen, H. cDNA cloning and expression of a novel human UDP–N–acetyl–alpha– D–galactosamine. Polypeptide N–acetylgalactosaminyltransferase, GalNAc–t3. *J. Biol. Chem.* 271:17006–17012, 1996.

Breton, C., Bettler, E., Joziasse, D.H., Geremia, R.A. and Imberty, A. Sequence–function relationships of prokaryotic and eukaryotic galactosyltransferases. *J Biochem* 123:1000–1009, 1998.

Clausen, H. and Hakomori, S. ABH and related histo–blood group antigens; immunochemical differences in carrier isotypes and their distribution. *Vox Sanguinis* 56:1–20, 1989.

Clausen, H., White, T., Takio, K., et al. Isolation to homogeneity and partial characterization of a histo–blood group A defined Fuc alpha 1—2Gal alpha 1—3–N–acetylgalactosaminyltransferase from human lung tissue. *J. Biol. Chem.* 265:1139–1145, 1990.

Hakomori, S. Aberrant glycosylation in tumors and tumor–associated carbohydrate antigens. Tumor malignancy defined by aberrant glycosylation and sphingo(glyco)lipid metabolism. *Advances in Cancer Research* 52:257–331, 1989.

Hakomori, S. Tumor malignancy defined by aberrant glycosylation and sphingo(glyco)lipid metabolism. *Cancer Res* 56:5309–5318, 1996.

Hennett, T., Dinter, A., Kuhnert, P., Mattu, T.S., Rudd, P.M. and Berger, E.G. Genomic cloning and expression of three murine UDP–galactose: –N–acetylglucosamine 1,3–galactosyltransferase genes. *J. Biol. Chem.* 273:58–65, 1998.

Holmes, E.H. Characterization and membrane organization of beta 1—3– beta 1—4–galactosyltransferases from human colonic adenocarcinoma cell lines Cob 205 and 5W403: basis for preferential synthesis of type 1 chain lacto–series carbohydrate structures. *Arch Biochem Biophys* 270:630–646, 1989.

Isshiki S, Togayachi A, Kudo T, Nishihara S, Watanabe M, Kubota T, Kitajima M, Shiraishi N, Sasaki K, Andoh T, Narimatsu H. Cloning, expression, and characterization of a novel UDP–galactose:beta–N–acetylglucosamine beta 1,3–galactosyltransferase (beta3Gal–T5) responsible for synthesis of type 1 chain in colorectal and pancreatic epithelia and tumor cells derived therefrom. *J Biol Chem.* 274(18):12499–507, 1999.

Kannagi, R., Levery, S.B., Ishigami, F., et al. New globosides glycosphingolipids in human teratocarcinoma reactive with the monoclonal antibody directed to a developmentally regulated antigen, stage–specific embryonic antigen 3. *J. Biol. Chem.* 258:8934–8942, 1983.

Kobata. A. Structures and functions of the sugar chains of glycoproteins. *Eur J Biochem* 209:483–501, 1992.

Kolbinger, F., Streiff, M.B. and Katopodis, A.G. Cloning of a human UDP–galactose:2–acetamido–2–deoxy–D–glucose 3 –galactosyltransferase catalysing the formation of type 1 chains. *J. Biol. Chem.* 273:433–440, 1998.

Mårtensson, S., Levery, S.B., Fang, T. and Bendiak, B. Neutral core oligosaccharides of bovine submaxillary mucin. Use of lead tetraacetate in the cold for establishing branch positions. *Eur. J. Biochem.* 258(2):603–22, 1998.

Miyazaki, H., Fukumoto, S., Okada, M., Hasegawa, T. and Furukawa, K. Expression cloning of rat cdna encoding UDP–galactose G(d2) 1,3 galactosyltransferase that determines the expression of G(D1 b)/G(M1)G(A1). *J. Biol. Chem.* 272:24794–24799, 1997.

Okajima T, Nakamura Y, Uchikawa M, Haslam DB, Numata SI, Furukawa K, Urano T, Furukawa K. Expression cloning of human globoside synthase cDNAs. Identification of beta 3Gal–T3 as UDP–N–acetylgalactosamine:globotriaosylceramide beta 1,3–N–acetylgalactosaminyltransferase. *J Biol Chem.* 275(51):40498–503, 2000.

Oriol, R., Le Pendu, J. and Mollicone, R. Genetics of ABO, H, Lewis, X and related antigens. *Vox Sanguinis* 51:161–171, 1986.

Pollex–Kruger, A., Meyer, B., Stuike–Pill, R., Sinnwell, V., Matta, K.L. and Brockhausen, I. Preferred conformations and dynamics of five core structures of mucin type O–glycans determined by NMR spectroscopy and force field calculations. *Glycoconjugate J* 10:365–380, 1993.

Schwientek, T., Almeida, R., Levery, S.B., Holmes, E., Bennett, E.P. and Clausen, H. Cloning of a novel member of the UDP–galactose: –N–acetylglucosamine 1 ,4–galactosyltransferase family, 4Gal–T4, involved in glycosphingolipid biosynthesis. *J. Biol Chem.* 273:29295–29305, 1998.

Seko, A., Ohkura, T., Kitamura, H., Yonezawa, S., Sato, E. and Yamashita, K. Quantitative differences in GlcNAc:betal—>3 and GlcNAc:beta1—>4 galactosyltransferase activities between human colonic adenocarcinomas and normal colonic mucosa. *Cancer Res* 56:3468–3473, 1996.

Sheares, B.T. and Carlson, D.M. Characterization of UDP–galactose:2–acetamido–2–deoxy–D– glucose 3 beta–galactosyltransferase from pig trachea. *J. Biol. Chem.* 258:9893–9898, 1983.

Sheares, B.T., Lau, J.T. and Carlson, D.M. Biosynthesis of galactosyl–beta 1,3–N– acetylglucosamine. *J. Biol. Chem.* 257:599–602, 1982.

Shiraishi N, Natsume A, Togayachi A, Endo T, Akashima T, Yamada Y, Imai N, Nakagawa S, Koizumi S, Sekine S, Narimatsu H, Sasaki K. Identification and characterization of three novel beta 1,3–N–acetylglucosaminyltransferases structurally related to the beta 1,3–galactosyltransferase family. *J Biol Chem.* 276(5):3498–507, 2001.

Sutherlin, M.E., Nishimori, I., Caffrey, T., et al. Expression of three UDP–N–acetyl–alpha–D galactosamine:polypeptide GalNAc N–acetylgalactosaminyltransferases in adenocarcinoma cell lines. *Cancer Res* 57:4744–4748, 1997.

Wandall, H.H., Hassan, H., Mirgorodskaya, E., et al. Substrate specificities of three members of the human UDP–N–acetyl–alpha–D–galactosamine:Polypeptide Nacetylgalactosaminyltransferase family, GalNAc–T1,–T2, and –T3. *J. Biol. Chem.* 272:23503–23514, 1997.

Wiggins, C.A.R. and Munro, S. Activity of the yeast MNN1alfa–1,3–mannosyltransferase requires a motif conserved in many other families of glycosyltransferases. *Proc. Natl. Acad. Sci.* USA 95:7945–7950, 1998.

Zhou D, Henion TR, Jungalwala FB, Berger EG, Hennet T. The beta 1,3–galactosyltransferase beta 3GalT–V is a stage–specific embryonic antigen–3 (SSEA–3) synthase. *J Biol Chem.* 275(30):22631–4, 2000.

Genbank Accession No. AB020337, Isshiki et al., May 14, 1999.

Genbank Accession No. NM_006057, Amado et al, Jun. 24, 1999.

Genbank Accession No. AJ003597, Yaspo Dec. 4, 1997.

Genbank Accession No. AF064860, Hattori et al, Jun. 2, 1998.

\* cited by examiner

β3Gal-T5

```
-78  CCACCTCAGCCTCCTAGCATAAAACTAGACACATCCTCATGCTTTTGAGGTCTAATCATTGGATTTTGTTCCTTTCAG      -1

1         M  A  F  P  K  M  R  L  M  Y  I  C  L  L  V  L  G  A  L  C  L  Y  P  S  M  Y       26
1    ATGGCTTTCCCGAAGATGAGATTGATGTATATCTGCCTTCTGGTTCTGGGGGCTCTTTGTTTGTATTTTAGCATGTAC       78

27        S  L  N  P  F  K  E  Q  S  F  V  Y  K  K  D  G  N  F  L  K  L  P  D  T  D  C       52
79   AGTCTAAATCCTTTCAAAGAACAGTCCTTTGTTTACAAGAAAGACGGGAACTTCCTTAAGCTCCCAGATACAGACTGC      156

53        R  Q  T  P  P  F  L  V  L  L  V  T  S  S  H  K  Q  L  A  E  R  M  A  I  R  Q       78
157  AGGCAGACACCTCCCTTCCTCGTCCTGCTGGTGACCTCATCCCACAAACAGTTGGCTGAGCGCATGGCCATCCGGCAG      234

79        T  W  G  K  E  R  T  V  K  G  K  Q  L  K  T  F  F  L  L  G  T  T  S  S  A  A      104
235  ACGTGGGGGAAAGAGAGGACGGTGAAGGGAAAGCAGCTGAAGACATTCTTCCTCCTGGGGACCACCAGCAGTGCAGCG      312

105       E  T  K  E  V  D  Q  E  S  Q  R  H  G  D  I  I  Q  K  D  F  L  D  V  Y  Y  N*     130
313  GAAACAAAAGAGGTGGACCAGGAGAGCCAGCGACACGGGGACATTATCCAGAAGGATTTCCTAGACGTCTATTACAAT      390

131       L  T  L  K  T  M  M  G  I  E  W  V  H  R  F  C  P  Q  A  A  F  V  M  K  T  D      156
391  CTGACCCTGAAGACCATGATGGGCATAGAATGGGTCCATCGCTTTTGTCCTCAGGCGGCGTTTGTGATGAAAACAGAC      468

157       S  D  M  F  I  N  V  D  Y  L  T  E  L  L  L  K  K  N* R  T  T  R  F  F  T  G      182
469  TCAGACATGTTCATCAATGTTGACTATCTGACTGAACTGCTTCTGAAGAAAAACAGAACAACCAGGTTTTTCACTGGC      546

183       F  L  K  L  N  E  F  P  I  R  Q  P  F  S  K  W  F  V  S  K  S  E  Y  P  W  D      208
547  TTCTTGAAACTCAATGAGTTTCCCATCAGGCAGCCATTCAGCAAGTGGTTTGTCAGTAAATCTGAATATCCGTGGGAC      624

209       R  Y  P  P  F  C  S  G  T  G  Y  V  F  S  G  D  V  A  S  Q  V  Y  N* V  S  K      234
625  AGGTACCCACCATTCTGCTCCGGCACCGGCTACGTGTTTTCTGGCGACGTGGCGAGTCAGGTGTACAATGTCTCCAAG      702

235       S  V  P  Y  I  K  L  E  D  V  F  V  G  L  C  L  E  R  L  N  I  R  L  E  E  L      260
703  AGCGTCCCATACATTAAACTGGAAGACGTGTTTGTGGGGCTCTGCCTCGAAAGGCTGAACATCAGATTGGAGGAGCTC      780

261       H  S  Q  P  T  F  F  P  G  G  L  R  F  S  V  C  L  F  R  R  I  V  A  C  H  F      286
781  CACTCCCAGCCGACCTTTTTTCCAGGGGGCTTACGCTTCTCCGTATGCCTCTTCAGGAGGATCGTGGCCTGCCACTTC      858

287       I  K  P  R  T  L  L  D  Y  W  Q  A  L  E  N  S  R  G  E  D  C  P  P  V  *         310
859  ATCAAGCCTCGGACTCTCTTGGACTACTGGCAGGCTCTAGAGAATTCCCGGGGGGAAGATTGTCCGCCTGTCTGA...      933
```

UDP-GALACTOSE: β-N-ACETYL-GLUCOSAMINE β1, 3GALACTOSYLTRANSFERASES, β3GAL-T5

This invention claims priority in the United States under 35 U.S.C. §119 to Denmark Application No. PA 1998 01483 filed Nov. 13, 1998, which application is incorporated by reference herein in its entirety.

1. FIELD OF THE INVENTION

The present invention relates generally to the biosynthesis of glycans found as free oligosaccharides or covalently bound to proteins and glycosphingolipids. This invention is more particularly related to a family of nucleic acids encoding UDP-D-galactose:βN-acetylglucosamine β1,3-galactosyltransferases (β3Gal-transferases), which add galactose to the hydroxy group at carbon 3 of 2-acetamido-2-deoxy-D-glucose (GlcNAc). This invention is more particularly related to a gene encoding the fifth member of the family of β3Gal-transferases, termed β3Gal-T5, probes to the DNA encoding P3Gal-T5, DNA constructs comprising DNA encoding β3Gal-T5, recombinant plasmids and recombinant methods for producing β3Gal-T5, recombinant methods for stably transfecting cells for expression of β3Gal-T5, and methods for indication of DNA polymorphism in patients.

2. BACKGROUND OF THE INVENTION

A family of UDP-galactose; β-N-acety -glucosamine β1-3galactosyl-transferases (β3Gal-T's) was recently identified (Amado, M., Almeida, R., Carneiro, F., et al. A family of human β3-gal actosyltransferases: characterisation of four members of a UDP-galactose β-N-acetylglucosamine/ β-N-acetylgalactosamine β1,3-Galactosyltransferase family. *J. Biol. Chem.* 273:12770–12778, 1998; Kolbinger, F., Streiff, M. B. and Katopodis, A. G. Cloning of a human UDP-galactose:2-acetamido-2-deoxy-D-glucose β3-galactosyltransferase catalysing the formation of type 1 chains. *J. Biol. Chem.* 273:433–440, 1998; Hennett, T., Dinter, A., Kuhnert, P., Mattu, T. S., Rudd, P. M. and Berger, E. G. Genomic cloning and expression of three murine UDP-galactose: β-N-acetylglucosamine β1,3-galactosyltransferase genes. *J. Biol. Chem.* 273:58–65, 1998; Miyaki, H., Fukumoto, S., Okada, M., Hasegawa, T. and Furukawa, K. Expression cloning of rat cDNA encoding UDP-galactose G(D2) β1,3 galactosyltransferase that determines the expression of G(D1b)/G(M 1)G(A1). *J. Biol. Chem.* 272:24794–24799, 1997). Three genes within this family, β3Gal-T1, -T2, and -T3, encode β3gal actosyltransferases that form the Galβ1-3GlcNAc linkage. The type 1chain Galβ1-3GlcNAc sequence is found in both N- and O-linked oligosaccharides of glycoproteins and in lacto-series glycosphingolipids, where it is the counterpart of type 2 Galβ1-4GlcNAc poly-N-acetyllactosainine structures (Kobata. A. Structures and functions of the sugar chains of glycoproteins. *Eur J Biochem* 209:483–501, 1992.). Type 1 chain structures are found mainly in endodermally derived epithelia, whereas the type 2 chains are found in ecto- and mesodermally derived cells including erythrocytes (Oriol, R., Le Pendu, J. and Mollicone, R. Genetics of ABO, H, Lewis, X and related antigens. *Vox Sanguinis* 51:161–171, 1986; Clausen, H. and Hakomori, S. ABH and related histo-blood group antigens; immunochemical differences in carrier isotypes and their distribution. *Vox Sanguinis* 56:1–20, 1989). Normal gastro-intestinal epithelia express mainly type 1 chain glycoconjugates, while type 2 chain structures are predominantly expressed in tumors (Hakomori, S. Aberrant glycosylation in tumors and tumor-associated carbohydrate antigens. Tumor malignancy defined by aberrant glycosylation and sphingo(glyco)lipid metabolism. *Advances in Cancer Research* 52:257–331, 1989; Hakomori, S. Tumor malignancy defined by aberrant glycosylation and sphingo(glyco)lipid metabolism. *Cancer Res* 56:5309–5318, 1996). It is of considerable interest to define the gene(s) responsible for formation of these core structures in normal and malignant epithelia. Several characteristics of the three previously described β3Gal-Ts capable of forming type 1 chain structures suggest that these are not the major enzyme(s) involved in type 1 chains synthesis in epithelia: (i) Northern analysis indicates that β3Gal-T1 and -T2 are exclusively expressed in brain (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998; Kolbinger, F., Streiff, M. B. and Ktopodis, A. G. Cloning of a human UDP-galactose:2-acetamido-2-deoxy-D-glucose β3-galactosyltransferase catalysing the formation of type 1 chains. *J. Biol. Chem.* 273:433–440, 1998; Hennett, T., Dinter, A., Kubnert, P., Mattu, T. S., Rudd, P. M. and Berger, E. G. Genomic cloning and expression of three murine UDP-galactose: β-N-acetylglucosamine/β1,3-galactosyltransferase genes. *J. Biol. Chem.* 273:58–65, 1998); (ii) although β3Gal-T3 has a wider expression pattern it is not detected in several tissues including colon and it is weakly expressed in gastric mucosa (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998; Kolbinger, F., Streiff, M. B. and Ktopodis, A G. Cloning of a human T.JDP-galactose:2-acetamido-2-deoxy-D-glucose β3-galactosyltransferase catalysing the formation of type 1 chains. *J. Biol. Chem.* 273:433–440, 1998); (iii) the kinetic properties of recombinant enzymes are not consistent with those reported for βGal-T activities in epithelia (Sheares, B. T., Lau, J. T. and Carlson, D. M. Biosynthesis of galactosyl-beta β1,3-N-acetylgiucosamine. *J. Biol. Chem.* 257:599–602, 1982; Holmes, E. H. Characterization and membrane organization of beta 1–3 and beta 1–4 galacto-syltransferases from human colonic adenocarcinoma cell lines Cob 205 and SW403: basis for preferential synthesis of type 1 chain lacto-series carbohydrate structures. *Arch Biochem Biophys* 270:630–646, 1989); and (iv) the acceptor substrate specificities of β3Gal-T1, -T2, or -T3 do not include the mucin-type core 3 structure (Amado, M., Almeida, R., Cameiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998; Hennett, T., Dinter, A., Kuhnert, P., Mattu, T. S., Rudd, P. M. and Berger, E. G. Genomic cloning and expression of three murine UDP-galactose: β3-N-acetylglucosamine β1,3-galactosyltransferase genes. *J. Biol. Chem.* 273:58–65, 1998), which was previously found to be a highly efficient substrate for β3Gal-T activity isolated from porcine trachea (Sheares, B. T. and Carison, D. M. Characterization of UDP-galactose:2-acetamido-2-deoxy-D-glucose 3 beta-galactosyltransferase from pig trachea. *J. Biol. Chem.* 25 8:9893–9898, 1983).

Access to additional existing βGlcNAc β3Gal-transferase genes encoding β3Gal-transferases with better kinetic properties than β3Gal-T1, -T2, and -T3 would allow production of more efficient enzymes for use in galactosylation of oligosaccharides, glycoproteins, and glycosphingolipids. Such enzymes could be used, for example, in pharmaceutical or other commercial applications that require synthetic galactosylation of these or other substrates that are not or poorly acted upon by β3Gal-T1, -T2, and -T3, in order to produce appropriately glycosylated glycoconjugates having particular enzymatic, immunogenic, or other biological and/or physical properties.

Consequently, there exists a need in the art for additional isolated UDP-galactose: β3-N-acetyl-glucosamine β1-3-Galactosyltransferases having unique, specific properties and the primary structure of the genes encoding these enzymes. The present invention meets this need, and further presents other related advantages, as described in detail below.

3. SUMMARY OF THE INVENTION

The present invention provides isolated nucleic acids encoding human UDP-galactose: β3-N-acetylglucosamine β1,3-galactosyltransferase (β3Gal-T5), including cDNA and genomic DNA. ⊖3Gal-T5 has better kinetic properties than β3Gal-T1, -T2, and T3, as exemplified by its better activity with saccharide derivatives and glycoprotein substrates as well as its activity with globoside glycolipid. Indeed, β3Gal-T5 is the first glycosyltransferase available for transfer of Gal β1-3 to globoside (GalNAcβ1-3Galα1-4Galβ1-4Glcβ1-Cer). The complete nucleotide sequence of β3Gal-T5, is set forth in FIG. 1.

In one aspect, the invention encompasses isolated nucleic acids comprising or consisting of the nucleotide sequence of nucleotides 1–933 as set forth in FIG. 1, or sequence-conservative or function-conservative variants thereof. Also provided are isolated nucleic acids hybridizable with nucleic acids having the sequence as set forth in FIG. 1 or fragments thereof or sequence-conservative or function-conservative variants thereof. In various embodiments, the nucleic acids of the invention are hybridizable with β3Gal-T5 sequences under conditions of low stringency, intermediate stringency, high stringency, or specific preferred stringency conditions defined herein. In one embodiment, the DNA sequence encodes the amino acid sequence, as set forth in FIG. 1, from methionine (amino acid no. 1) to valine (amino acid no. 310). In another embodiment, the DNA sequence encodes an amino acid sequence comprising a sequence from methionine (no. 25) to valine (no. 310) as set forth in FIG. 1.

In a related aspect, the invention provides nucleic acid vectors comprising β3Gal-T5 DNA sequences, including but not limited to those vectors in which the β3Gal-T5 DNA sequence is operably linked to a transcriptional regulatory element (e.g. a promoter, an enhances, or both), with or without a polyadenylation sequence. Cells comprising these vectors are also provided, including without limitation transiently and stably expressing cells. Viruses, including bacteriophages, comprising β3Gal-T5-derived DNA sequences are also provided. The invention also encompasses methods for producing β3Gal-T5 polypeptides. Cell-based methods include without limitation those comprising: introducing into a host cell an isolated DNA molecule encoding β3Gal-T5, or a DNA construct comprising a DNA sequence encoding β3Gal-T5; growing the host cell under conditions suitable for β3Gal-T5 expression; and isolating β3Gal-T5 produced by the host cell. Further, this invention provides a method for generating a host cell with de novo stable expression of β3Gal-T5 comprising: introducing into a host cell an isolated DNA molecule encoding β3Gal-T5 or an enzymatically-active fragment thereof (such as, for example, a polypeptide comprising amino acids 25–310 as set forth in FIG. 1), or a DNA construct comprising a DNA sequence encoding β3Gal-T5 or an enzymatically active fragment thereof; selecting and growing host cells in an appropriate medium; and identifying stably transfected cells expressing β3Gal-T5. The stably transfected cells may be used for the production of β33Gal-T5 enzyme for use as a catalyst and for recombinant production of peptides or proteins with appropriate galactosylation. For example, eukaryotic cells, whether normal or diseased cells, having their glycosylation pattern modified by stable transfection as above, or components of such cells, may be used to deliver specific glycoforms of glycopeptides and glycoproteins, such as, for example, as immunogens for vaccination.

In yet another aspect, the invention provides isolated β3Gal-T5 polypeptides, including without limitation polypeptides having the sequence set forth in FIG. 1, polypeptides having the sequence of amino acids 25–310 as set forth in FIG. 1, and a fusion polypeptide consisting of at least amino acids 25–310 as set forth in FIG. 1 fused in frame to a second sequence, which may be any sequence that is compatible with retention of β3Gal-T5 enzymatic activity in the fusion polypeptide. Suitable second sequences include without limitation those comprising an affinity ligand, a reactive group, and/or a functional domain from another protein.

In another aspect of the present invention, methods are disclosed for screening for mutations in the coding region (exon I) of the β3Gal-T5 gene using genomic DNA isolated from, e.g., blood cells of normal and/or diseased subjects. In one embodiment, the method comprises: isolation of DNA from a normal or diseased subject; PCR amplification of coding exon I; DNA sequencing of amplified exon DNA fragments and establishing therefrom potential structural defects of the β3Gal-T5 gene associated with disease.

These and other aspects of the present invention will become evident upon reference to the following detailed description and drawings.

4. BRIEF DESCRIPTION OF THE DRAWINGS

FIG. 1 depicts the DNA sequence of the β3Gal-T5 gene (SEQ ID NO:8) and the predicted amino acid sequence of β3Gal-T5 (SEQ ID NO:9). The amino acid sequence is shown in single-letter amino acid code. The hydrophobic segment representing the putative transmembrane domain is underlined with a double line (Kyte & Doolittle, window of 8 (Kyte, J. and Doolittle, R. F. A simple method for displaying the hydropathic character of a protein. *Journal of Molecular Biology* 157:105–132, 1982)). Three consensus motifs for N-glycosylation are indicated by asterisks. The location of the primers used for preparation of the expression constructs are indicated by single underlining. The single-letter amino acid code corresponds to the three-letter amino acid code of the Sequence Listing set forth hereinbelow, as follows: A, Ala; R, Arg; N, Asn; D, Asp; B, Asx; C, Cys; Q, Gln; E, Glu; Z, Glx; G, Gly; H, His; I, Ile; L, Leu; K, Lys; M, Met; F, Phe; P, Pro; S, Ser; T, Thr; W, Trp; Y, Tyr; and V, Val.

Figure 2:
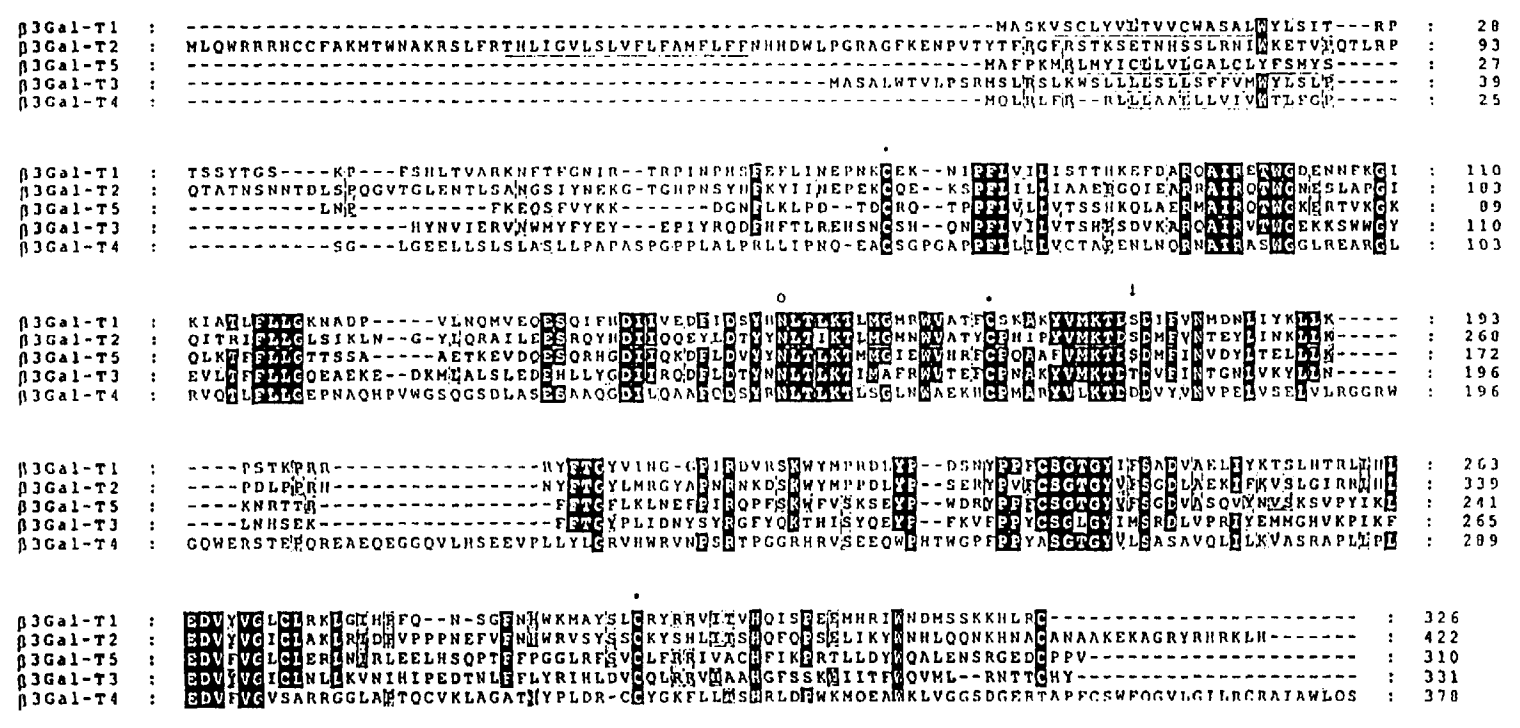

FIG. 2 is an illustration of multiple sequence analysis (ClustalW) of five human β3Gal-transferases. The transferases are listed according to order of similarity with β3Gal-T1. The SEQ ID NOs for the transferases shown are as follows: β3Gal-T1 (SEQ ID NO:11), β3Gal-T2 (SEQ ID NO:10), β3Gal-T3 (SEQ ID NO:12), β3Gal-T4 (SEQ ID NO:13) and β3Gal-T5 (SEQ ID NO:9). Introduced gaps are shown as hyphens, and aligned identical residues are boxed (black for all sequences, dark grey for four sequences, and light grey for three sequences). The putative transmembrane domains are underlined with a single line. The positions of conserved cysteines are indicated by asterisks. One conserved N-glycosylation site is indicated by an open circle. The DxD motif is indicated by an arrow.

FIG. 3 is a schematic depiction of β3Gal-transferases aligned for the conserved cysteine residues. Potential N-glycosylation sites are indicated by trees. Cysteine residues are indicated by the letter C, and conservation of cysteines are indicated by stippled lines between genes. The position of conserved sequence motifs as shown in FIG. 2 are indicated with dotted lines and amino acid sequences. The putative transmembrane signal is indicated by thick lines.

Figure 4:
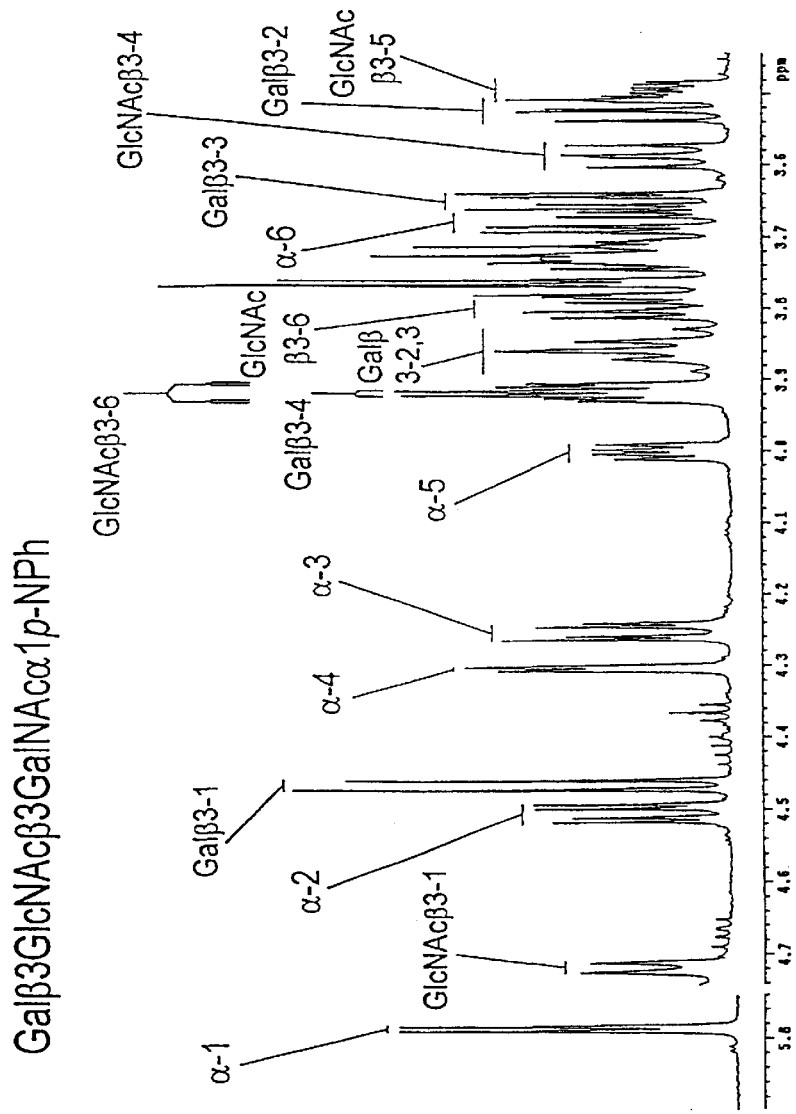

FIG. 4 depicts sections of a 1-D $^1$H-NMR spectrum of the β3Gal-T5 product with Core3-pNPh, Galβ1→3GlcNAcβ1→3GalNAcα1→1pNPh, showing all non-exchangeable monosaccharide ring methine and exocyclic methylene resonances. Residue designations for the Galβ1→3(Galβ3), GlcNAcβ1→3 (GlcNAcβ3), GalNAcα1→1(α) are followed by proton designations (Braunschweiler, L. and Ernst, R. R. Coherence transfer by isotropic mixing: Application to proton correlation spectroscopy. *J. Magn. Reson.* 53:521–528, 1983; Bax, A. and Davis, D. G. MLEV-1 7-based two-dimensional homonuclear magnetization transfer spectroscopy. *J. Magn. Reson.* 65:355–360, 1985a; Bothner-By, A. A., Stephens, R. L., Lee, J. M., Warren, C. D. and Jeanloz, R. W. Structure determination of a tetrasaccharide: Transient nuclear Overhauser effects in the rotating frame. *J. Am. Chem. Soc* 106:811–813, 1984; Bax, A. and Davis, D. G. Practical aspects of two-dimensional transverse NOE spectroscopy. *J. Magn. Reson.* 63:207–213, 1985b; Keeler, J., Laue, E. D. and Moskau, D. Experiments for recording pure-absorption heteronuclear correlation spectra using pulsed field gradients. *J. Magn. Reson.* 98:207–216, 1992; Bodenhausen, G. and Ruben, D. J. Natural abundance nitrogen-15 NMR by enhanced heteronuclear spectroscopy. *Chem. Phys. Lett.* 69:185–189, 1980).

Figure 5:

FIG. 5 is a photographic illustration of Northern blot analysis of human tumor cell lines. Human pancreatic adenocarcinoma cell lines AsPC-1, BxPC-3, Capan-1, Capan-2, Colo357, HPAF, PANC-1, Suit2, S2-013, and the HT29 colon adenocarcinoma cell line were probed with $^{32}$P-labeled cDNA of β3Gal-T5 corresponding to the soluble expression construct. 5. DETAILED DESCRIPTION OF THE INVENTION All patent applications, patents, and literature references cited in this specification are hereby incorporated by reference in their entirety. In the case of conflict, the present description, including definitions, is intended to control.

5.1. Definitions

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in an mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.)

In one embodiment, this invention provides nucleic acids which are hybridizable to a β3Gal-T5 nucleic acid under the following hybridization conditions: a full-length or soluble β3Gal-T5 expression construct (see Examples) is used as probe (e.g. by random primed labeling) against a DNA or RNA blot, the blot is probed overnight at 42° C. as previously described (Bennett et al., 1996, cDNA cloning and expression of a novel human UDP-N-acetyl-alpha-D-galactosamine, Polypeptide N-acetyl-galactosaminyltransferase, GalNAc-T3, *J. Biol. Chem.* 2. 271, 17006–17012), washed 2×10 min at room temperature (RT; from 18 to 23° C.) with 2×SSC, 1% Na$_4$P$_2$O$_2$, 2×20 min at room 0.2×SSC, 1% SDS, 1% Na$_4$P$_2$O$_2$ and once 10 min with 0.2×SSC at RT ("preferred hybridization conditions"). Under these preferred hybridization conditions, there is no cross-hybridization between β3Gal-T5 and the previously-identified β3Gal-Ts (i.e. β3Gal-T1, -T2, -T3, and T4; see also Amado et al., 1998, A family of human β3-galactosyltransferases: characterization of four members of a UDP-galactose β-N-acetylglucosamine/β-N-acetylgalactosamine β1,3-Galactosyltransferase family, *J. Biol. Chem.* 273, 12770–12778).

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants". and "function-conservative variants". Sequence-conservative variants are those in which a change of one or more nucleotides in a given codon position results in no alteration in the amino acid encoded at that position. Function-conservative variants of β3Gal-T5. are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., a galactosyltransferase and that contributes a galactosyl moiety for the transferase reaction. For β3Gal-T5, a donor substrate is UDP-galactose. An "acceptor substrate" is a molecule, preferably a saccharide or oligosaccharide, that is recognized by, e.g., a galatosyltransferase and that is the target for the modification catalyzed by the transferase, i.e., receives the galatosyl moiety. For β3Gal-T5, acceptor substrates include without limitation oligosaccharides, glycoproteins, O-linked GIeNAc-glycopeptides, O-linked GalNAc-glycopeptides, and glycosphingolipids containing the sequences, GlcNAcβ1-6Gal, GlcNAcβ1-6GaINAc, GlcNAcβ1-3 GalNAc, GlcNAcβ1-2Man, GlcNAcβ1-4Man, GlcNAcβ1-6Man, GlcNAcβ1-3Man, Glcβ1-ceramide, and GalNAcβ1-3Gal.

The present invention provides the isolated DNA molecules, including genomic DNA and cDNA, encoding the UDP-galactose: β-N-acetylglucosamine β1,3-galactosyltransferase (β3Gal-T5).

β3Gal-T5 was identified by analysis of EST database sequence information, and cloned based on EST and 5'RACE cDNA clones. The cloning strategy may be briefly summarized as follows: 1) synthesis of oligonucleotides derived from EST sequence information, designated EBER1301 and EBER 1302; 2) PCR screening and isolation of a P1 genomic DNA phage containing the entire coding region of β3Gal-T5; 3) sequencing of P1 DNA; 4) identification of a novel DNA sequence corresponding to β3Gal-T5; 5) construction of expression constructs by reverse-transcription-polymerase chain reaction (RT-PCR) using human P1 DNA; 6) expression of the cDNA encoding β3Gal-T5 in Sf9 (*Spodoptera frugiperda*) cells. More specifically, the isolation of a representative DNA molecule encoding a novel fifth member of the mammalian UDP-galactose: β-N-acetylglucosamine/β-N-acetylgalactosamine β1,3-galactosyltransferase family involved the following procedures described below.

5.2. Identification and Cloning of Human β3Gal-T5

A novel gene, with significant sequence similarity to the β3Gal-transferase gene family was identified (FIG. 1), using the strategy as previously described (Almeida, R., Amado, M., David, L., et al. A Family of Human β4-Galactosyltransferases: Cloning and expression of two novel UDP-Galactose β-N-Acetylglucosamine β1,4-Galactosyl-transferases, β4Gal-T2 and β4Gal-T3. *J.Biol.Chem.* 272:31979–31992, 1997). The predicted coding region of β3Gal-T5 included two potential initiation codons, preceding a hydrophobic sequence, of which the second is in agreement with Kozak's rule (Kozak, M. Regulation of translation in eukaryotic systems. *Ann Rev Cell Biol* 8:197–225, 1992) (FIG. 1). The predicted coding sequence indicates that β3Gal-T5 is an type II transmembrane glycoprotein with a N-terminal cytoplasmic domain of 2 or 7 residues, a transmembrane segment of 19 residues flanked by charged residues, and a stem region and catalytic domain of 284 residues with three potential N-glycosylation sites (FIG. 1). A Kyte and Doolittle hydropathy plot (Kyte, J. and Doolittle, R. F. A simple method for displaying the hydropathic character of a protein. *Journal of Molecular Biology* 157:105–132, 1982) indicated that the putative stem region was hydrophilic similar to βGal-T1, -T2 and -T3 (Amado, M., Almeida, R., Cameiro, F., et al. A family of human β3-galactosyltransferases: characterization of four members of a UDP-galactose β-N-acetylglucosamine/β-N-acetylgalactosamine β1,3-Galactosyltransferase family. *J. Biol. Chem.* 273:12770–12778, 1998). In contrast, p3Gal-T4, with exclusive glycolipid specificity has a hydrophobic stem region (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998; Miyaki, H., Fukumoto, S., Okada, M., Hasegawa, T. and Furukawa, K. Expression cloning of rat cdna encoding UDP-galactose G(D2) β1,3 galactosyltransferase that determines the expression of G(D1b)/G(M 1)G(A1). *J. Biol. Chem.* 272:24794–24799, 1997).

A multiple sequence alignment of five β3Gal-transferases is shown in FIG. 2. The β3Gal-T5 gene has highest similarity to β3Gal-T2. Similarities among the five human genes are found predominantly in the central regions; there were no significant similarities in the $NH_2$-terminal regions. Several motifs in the putative catalytic domains are conserved between all the sequences. Noteworthy, three cysteine residues are aligned within all the human genes, and three additional are aligned within β3Gal-T1, -T2, -T3 and -T5 (FIG. 2, FIG. 3). One potential N-linked glycosylation site, occurs in the central region of the putative catalytic domains, and is conserved in all sequences. Similarly, a single N-linked glycosylation site was conserved among all members of β4Gal-T gene family (Schwientek, T., Almeida, R., Levery, S. B., Holmes, E., Bennett, E. P. and Clausen, H. Cloning of a novel member of the UDP-galactose: β-N-acetylglucosamine β1,4-galactosyltransferase family, β4Gal-T4, involved in glycosphingolipid biosynthesis. *J. Biol Chem.* 273:29295–29305, 1998 Schwientek et al., 1998). The DXD motif, recently shown to be conserved among several glycosyltransferases gene families (Wiggins, C. A. R. and Munro, S. Activity of the yeast MNN1alfa-1, 3-mannosyltransferase requires a motif conserved in many other families of glycosyltransferases. *Proc. Natl. Acad. Sci. USA* 95:7945–7950, 1998; Breton, C., Bettler, E., Joziasse, D. H., Geremia, R. A. and Imberty, A. Sequence-function relationships of prokaryotic and eukaryotic galactosyltransferases. *J Biochem* 123:1000–1009, 1998), is also present in all human β3Gal-transferases.

5.3. Genomic Organization and Chromosomal Localization of β3GAL-T5, BGALT5

The coding region of β3Gal-T5 was determined by sequencing of P1 clones to be located in a single exon, similar to βGal-T1, -T2, -T3 and -T4 (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998). This was confirmed in a recently released 164 kb genomic sequence (GenBank accession number AF064860). BGALT5 is located on chromosome 21 q22.3. The other three genes in the family are located on different chromosomes BGALT2 (1q31), -T3 (3q25), and -T4 (6p21.3) (Amado, M., Almeida, R., Carneiro, F., et al. A family of human β3-galactosyltransferases: characterisation of four members of a UDP-galactose β-N-acetylglucosarnine/β-N-acetylgalactosamine β1,3-Galactosyltransferase family. *J. Biol. Chem.* 273:12770–12778, 1998).

5.4. Expression of β3GAL-T5 in Insect Cells

Expression of a soluble construct of β3Gal-T5 in Sf9 cells resulted in a marked increase (20–30 fold) in galactosyltransferase activity using acceptor substrates containing terminal βGlcNAc, when compared to uninfected cells or cells infected with irrelevant constructs (not shown). Analysis of the substrate specificity of partially purified β3Gal-T5 activity showed that all effective substrates contained βGlcNAc at the nonreducing end (Table I).

TABLE I

Substrate specificity of β3Gal-T5 with saccharide acceptors

| Substrate concentration | β3Gal-T5[a] | |
|---|---|---|
| | 1 mM | 5 mM |
| | nmol/min/ml | |
| D-GlcNAc | 0.5 | 1.2 |
| β-D-GlcNAc-Bzl[b] | 1.5 | 3.9 |
| β-D-GlcNAc-1-p-Nph | 2.1 | 6.9 |
| β-D-GlcNAc-1-thio-p-Nph | 1.1 | 3.4 |
| β-D-GlcNAc-Me-umb | 2.6 | 7.5 |
| β-D-GalNAc-Me-umb | 0.0 | 0.0 |
| α-D-GlcNAc-Bzl | 0.0 | 0.0 |
| α-D-GalNAc-Bzl | 0.0 | 0.0 |
| α-D-Gal-1-o-Nph | 0.0 | 0.0 |
| β-D-Gal-1-o-Nph | 0.0 | 0.0 |
| β-D-Glc-Me-umb | 0.0 | 0.0 |
| β-Gal-(1–4)-β-D-Xyl-1-Me-umb[c] | 0.0 | 0.0 |
| β-D-GlcNAc-(1–3)-β-D-Gal-1-Me | 27.4 | 87.4 |
| β-D-GlcNAc-(1–3)-α-D-GalNAc-p-Nph | 10.8 | 34.4 |
| β-D-GlcNAc-(1–6)-α-D-Man-1-Me | 4.0 | 13.0 |
| β-D-GlcNAc-(1–2)-α-D-Man | 0.0 | 3.0 |
| β-D-GlcNAc-(1–2)-α-D-Man-(1–3)-[β-D-GlcNAc-(1–2)-α-D-Man-(1–6)-]D-Man | 0.0 | 0.0 |

[a]Enzyme partially purified as described elsewhere herein.
[b]Bzl, benzyl; Me, methyl; Me-Umb, 4-methyl-umbelliferyl; Nph, nitrophenyl.
[c]prepared enzymatically using -62 -D-Xyl-l-Me-Umb and UDP-Gal as substrates (R. Almeida, H. Clausen, unpublished).

Among the simple saccharide derivatives tested disaccharide β-D-GlcNAc-(1-3)-β-D-Gal-1-Me was better than all other saccharide derivatives. This in contrast to β3Gal-T1 and -T2 which had very low relative activities with disaccharides used as substrates (Amado, M., Almeida, R., Cameiro, F., et al. A family of human βp3-galactosyltransferases: characterisation of four members of a UDP-galactose β-N-acetylglucosamine/β-N-acetylgalactosanine β1,3-Galactosyltransferase family. *J. Biol. Chem.* 273:12770–12778, 1998; Kolbinger, F., Streiff, M. B. and Ktopodis, A. G. Cloning of a human UDP-galactose:2-acetamido-2-deoxy-D-glucose 3β-galactosyltransferase catalysing the formation of type 1 chains. *J. Biol. Chem.* 273:433–440, 1998; Hennett, T., Dinter, A., Kuhnert, P., Mattu, T. S., Rudd, P. M. and Berger, E. G. Genomic cloning and expression of three murine UDP-galactose: β-N-acetylglucosamine β1,3-galactosyltransferase genes. *J. Biol. Chem.* 273:58–65, 1998). β3Gal-T5 showed poor activity with saccharide derivatives representing N-linked core structures, namely β-D-GlcNAc-(1-6)-α-Man-1-Me, biantennary pentasaccharide and β-D-GlcNAc-(1-2)-α-D-Man. Particularly striking was a high relative activity towards β-D-GlcNAc(1-3)-α-D-GalNAc-1-p-Nph, which represents the core 3 O-linked structure. A comparison of relative activities of several β3- and β4Gal-transferases with core 3 and core 2 O-linked structures is presented in Table II.

TABLE II

Activities with mucin-type core 2 and 3 acceptors

| | βGlcNAc-Bzl[b] | βGlcNAc(1,3)αGalNAc-p-Nph | | | | βGlcNac(1,6)[βGal(1,3)]αGalNAc-p-Nph | | | |
|---|---|---|---|---|---|---|---|---|---|
| | | 0.2 mM | | 2 mM | | 0.2 mM | | 2 mM | |
| | nmol/min | nmol/min | | | | nmol/min | | | |
| β3Gal-T1[a] | 0.03 | 0.0 | (0.0) | 0.0 | (0.0) | 0.0 | (0.0) | 0.0 | (0.0) |
| β3Gal-T2 | 0.04 | 0.0 | (0.0) | 0.0 | (0.0) | 0.0 | (0.0) | 0.0 | (0.0) |
| β3Gal-T5 | 0.1 | 0.3 | (0.3) | 0.2 | (2.0) | 0.0 | (0.0) | 0.01 | (0.1) |
| β4Gal-T2 | 0.03 | 0.2 | (0.6) | 0.01 | (0.3) | 0.03 | (1.0) | NA | |
| β4Gal-T3 | 0.03 | 0.1 | (0.3) | 0.03 | (1.0) | ND | | ND | |

[a]Enzyme partially purified as described elsewhere herein.
[b]β-D-GlcNAc-Bzl was used at 80 mM with β3Gal-T1 and β3Gal-T2; at 20 mM with β3Gal-T5; at 0.25 mM with β4Gal-T2 and at 2 mM with β4Gal-T3. ND, not determined. NA. not applicable due to inhibition. ( ), ratio between values obtained with core 2 or 3 and those obtained with βGlcNAc-Bzl.

None of the β3Gal-Ts utilize the core 2 substrate and only β3Gal-T5 catalyzed glycosylation of core 3 substrates. The two β4Gal-Ts tested showed lower activity than β3Gal-T5 with the core 3 substrate, however, direct comparison is not possible. Nevertheless, type 1 chain structures are found on core 3 (van Halbeek, H., Dorland, L., Vliegenthart, J. F. G., et al. Primary-structure determination of fourteen neutral oligosaccharides derived from bronchial-mucus glycoproteins of patients suffering from cystic fibrosis, employing 500-MHz 1H-NMR spectroscopy. *Eur J Biochem* 7–20, 1982), but to the best of our knowledge core 2 structures are always extended with type 2 chain N-acetylactosamine chains.

Analysis of β3Gal-Ts with glycoprotein acceptors (Table III) showed that β3Gal-T5 only used bovine submaxillary mucin which carries approximately 10% GlcNAc terminating core 3O-linked glycans (Martensson, S., Levery, S. B., Fang, T. and Bendiak, B. Neutral core oligosaccharides of bovine submaxillary mucin. Use of lead tetraacetate in the cold for establishing branch positions. *Eur. J. Biochem.* 258, 603–622, 1998).

TABLE III

Substrate specificity of β3galactosyl-transferases with glycoprotein acceptors

| Acceptor substrate* | β3Gal-T1 | | β3Gal-T2 | | β3Gal-T5 | |
|---|---|---|---|---|---|---|
| | mmol/min | | mmol/min | | mmol/min | |
| β-D-GlcNAc-Bzl | 0.03 | | 0.04 | | 0.1 | |
| Hen egg albumin | 0.0 | (0.0) | 0.02 | (0.5) | 0.0 | (0.0) |
| Asialo-agalacto-fetuin | 0.01 | (0.3) | 0.07 | (1.8) | 0.0 | (0.0) |
| Bovine submaxillary mucin | 0.0 | (0.0) | 0.0 | (0.0) | 0.04 | (0.4) |
| Orosomucoid | 0.0 | (0.0) | 0.0 | (0.0) | 0.0 | (0.0) |

*β-o-GlcNAc-Bzl was used at 80 mM for β3Gal-T1 and β3Gal-T2 and at 20 mM for β3Gal-T5; ( ), ratio between values obtained with glycoproteins and those obtained with β.-D-GlcNAc-Bzl.

As reported previously and in the present study β3 Gal-T2 utilized glycoproteins with N-linked glycans while β3Gal-T1 showed no or very low activity with glycoprotein acceptors (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998) (Table III). A similar differential specificity for glycoproteins is found among β4Gal-transferases, where β4Gal-T1, -T2, and -T3 catalyze glycosylation of to N-linked glycoproteins, but a novel member, β4Gal-T4, appears to be inactive with these substrates (Schwientek, T., Almeida, R., Levery, S. B., Holmes, E., Bennett, E. P. and Clausen, H. Cloning of a novel member of the UDP-galactose: β-N-acetylglucosamine β1,4-galactosyltransferase family, β4Gal-T4, involved in glycosphingolipid biosynthesis. *J. Biol. Chem.* 273:29295–29305, 1998).

Analysis of the catalytic activities with a panel of glycolipid substrates revealed that β3Gal-T5 has high activity with GlcNAcβ1-3Galβ1-4Glcβ1-Cer (Lc3), in either taurodeoxycholate or Triton CF-54 (Table IV).

TABLE IV

Substrate specificities with glycolipid acceptors

| | | β3Gal-T5[a] | |
|---|---|---|---|
| Acceptor substrate | | TDOC[b] | Triton CF-54 |
| | | μmol/h/mg | |
| GlcCer | (Glcβ1-Cer) | 0.04 | ND |
| LacCer | (Galβ1-4Glcβ1-Cer) | ND | ND |
| Gb$_3$ | (Galα1-4Galβ1-4Glcβ1-Cer) | ND | ND |
| Gβ$_4$ | (GalNAcβ1-3Galα1-4Galβ1-4Glcβ1-Cer) | 0.6 | 0.09 |
| Gg$_3$ | (GalNAcβ1-4Galβ1-4Glcβ1-Cer) | 0.09 | 0.005 |
| GM$_2$ | (GalNAcβ1-4(NeuAcα2-3)Galpβ1-4Glcβ1-Cer) | ND | ND |
| GM$_1$ | (Galβ1-3GalNAcβ1-4(NeuAcα2-3)Galβ1-4Glcβ1-Cer) | ND | ND |
| Lc$_3$ | (GlcNAcβ1-3Galβ1-4Glcβ1-Cer) | 4.4 | 3.6 |
| nLc$_4$ | (Galβ1-4GlcNAcβ1-3Galβ1-4Glcβ1-Cer) | ND | ND |
| nLC$_5$ | (GlcNAcβ1-3Galβ1-4GlcNAcβ1-3Galβ1-4Glcβ1-Cer) | 1.6 | 0.4 |

[a]Enzyme partially purified as described elsewhere herein and the specific protein concentration was estimated by SDS-PAGE to be 300 μg/ml.
[b]Assays were performed using 100 μg of taurodeoxycholate (TDOC) or Triton CF-54/100 μl of reaction mixture. ND, not detectable.

Activity was also found with nLc$_5$ but this was almost 3-fold lower than with Lc$_3$, and activity was significantly lower in Triton CF-54. Interestingly, considerable activity was observed with Gb$_4$ and there were detectable incorporation into GlcCer and Gg$_3$. The product formed with Gb$_4$ was characterized and found primarily to represent the expected Galβ1-3Gb$_4$ structure. The apparent Km of β3Gal-T5 for Lc$_3$Cer in the presence taurodeoxycholate was approximately 2 μM, but due to substrate inhibition this result was only based on data points at low concentrations.

The acceptor substrate specificity and kinetic properties of β3Gal-T5 are similar to a previously reported porcine tracheal β3Gal-transferase activity (Sheares, B. T. and Carlson, D. M. Characterization of UDP-galactose:2-acetamido-2-deoxy-D-glucose 3 beta-galactosyltransferase from pig trachea. *J. Biol. Chem.* 258:9893–9898, 1983) and human colonic β3Gal-transferase activity (Seko, A., Ohkura, T., Kitamura, H., Yonezawa, S., Sato, E. and Yamashita, K. Quantitative differences in GlcNAc:beta1-->3 and GlcNAc:beta1-->4 galactosyltransferase activities between human colonic adenocarcinomas and normal colonic mucosa. *Cancer Res* 56:3468–3473, 1996). Both the porcine and human β3Gal-transferase activities have apparent Kms for UDP-Gal of 200–220 μM using βGlcNAcβ1-3Gal (GalNAc) acceptor substrates, and the secreted recombinant β3Gal-T5 had an apparent Km of 169 μM (Table V).

TABLE V

Kinetic properties of β3Gal-T5

| | β3Gal-T5[a] | |
|---|---|---|
| Substrate[b] | Km | Vmax |
| | mM | pmol/min |
| UDP-Gal | 0.169 | 1422.2 |
| β-D-GlcNAc-Bzl | 20.4 | 873.4 |
| β-D-GlcNAc-(1–3)-α-D-GalNAc-p-Nph | 2.8 | 931.1 |
| β-D-GlcNAc-(1–3)-α-D-Gal-Me | 1.8 | 972.9 |

[a]Enzyme partially purified as described elsewhere herein.
[b]The concentrations used were 25–400 μM for UDP-Gal, 3.75–60 mM for β-D-GlcNAc-Bzl and 0.3125–5 mM for β-D-GlcNAc-(1–3)-α-D-GalNAc-p-Nph and β-D-GlcNAc(1–3)-α-D-Gal-Me.

These relatively high Kms for donor substrates are significantly different from those reported for βGal-T1 and -T2 (90 and 37 μM, respectively) (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998). Interestingly, activity of the full length coding construct of β3Gal-T5 analyzed in Triton CF-54 homogenates of infected insect cells showed a lower apparent Km of 33 μM for the donor substrate (not shown). The purified β3Gal-transferase activity analyzed by Sheares, et al. (Shears, B. T. and Carison, D. M. Characterization of UDP-galactose:2-acetamido-2-deoxy-D-glucose 3 beta-galactosyltransferase from pig trachea. *J. Biol. Chem.* 258:9893–9898, 1983) is, however, likely to represent a truncated proteolytically cleaved form that is often found with affinity-purified glycosyltransferase preparations (Clausen, H., White, T., Takio, K., et al. Isolation to homogeneity and partial characterization of a histo-blood group A defined Fuc alpha 1-2Gal alpha 1-3-N-acetylgalactosaminyltransferase from human lung tissue. *J. Biol. Chem.* 265:1139–1145, 1990). Moreover, Holmes (Holmes, E. H. Characterization and membrane organization of beta 1-3- and beta 1-4-galactosyltransferases from human colonic adenocarcinoma cell lines Cob 205 and SW403: basis for preferential synthesis of type 1 chain lacto-series carbohydrate structures. *Arch Biochem Biophys* 270:630–646, 1989) reported that non-purified β3Gal-T activity from Colo2O5 cells had an apparent Km for UDP-Gal of 48 μM using glycolipids as acceptor substrate. This preparation may contain both full and secreted forms of transferases. The recombinant full length form of β3Gal-T5 resembled the recombinant secreted form in all other aspects tested. The porcine β3Gal-transferase activity has an apparent Km for core 3 of 2.4 mM and β3Gal-T5 exhibited an apparent Km for core 3 of 2.8 mM. Holmes (Holmes, E. H. Characterization and membrane organization of beta 1-3- and beta 1-4-galactosyltransferases from human colonic adenocarcinoma cell lines Cob 205 and SW403: basis for preferential synthesis of type 1 chain lacto-series carbohydrate structures. *Arch Biochem Biophys* 270:630–646, 1989) reported a Km for Lc₃Cer of 13 μM for β3Gal-T activity from Colo2O5 cells. The best substrate identified for β3Gal-T5 was β-D-GlcNAc(1-3)-D-β-Gal-1-Me [apparent Km of 1.8 mM (Table V)]. This is similar to the apparent Km of 2.9 mM for human colonic β3 Gal-T activity for β-D-GlcNAc (1-3)-D-β-Gal(1-4)-D-β-Glc (Seko, A., Ohkura, T., Kitamura, H., Yonezawa, S., Sato, E. and Yamashita, K. Quantitative differences in GlcNAc:betal-->3 and GlcNAc:betal-->4 galactosyltransferase activities between human colonic adenocarcinomas and normal colonic mucosa. *Cancer Res* 56:3468–3473, 1996). β3Gal-T5 showed strict donor substrate specificity for UDP-Gal and did not utilize UDP-GalNAc or UDPGlcNAc with the acceptor substrates tested (data not shown).

Expression of the full coding construct of β3Gal-T5 in Sf9 cells 60 hours postinfection resulted in virtually all β3Gal-transferase activity retained on cells (Table VI).

TABLE VI

Expression of full coding constructs of β3Gal-T1 and β3Gal-T5

|  | β3Gal-T1[b] | | β3Gal-T5 | |
| --- | --- | --- | --- | --- |
|  | Cells | Media | Cells | Media |
|  | nmol/min/ml | | nmol/min/ml | |
| β-D-GlcNAc-[a] | 7.2 | 0.2 | 1.5 | 0.1 |

[a]β-D-GlcNAcBzl was used at 20 mM.
[b]Enzyme sources were media or 1% Triton CF54 cell homogenates from βGal-T1 and -T5 transfected Sf9 cells, harvested 60 hrs post-infection.

This was also found for β3Gal-T1 (Table VI), and the same has been found for the other β3Gal-Ts as well as for a number of β4Gal-Ts and polypeptide GalNAc-transferases (not shown). In contrast, more than 50% of the enzyme activity is found in the media after 60 hours of transfection when truncated secreted constructs are used.

5.5. $^{1}$H- and $^{13}$C-NMR Spectroscopy of Product Formed Glycosylation of Core3-p-NPh with β3GAL-T5

The product derived from reaction of β3Gal-T5 with GlcNAcβ1-3GalNAcα1-1pNp was characterized by NMR spectroscopy to confirm that the proper linkage was formed between the donor sugar and the acceptor substrate. Comparison of a 1-D $^{1}$H-NMR spectrum of the product (FIG. 4) with that of the substrate (not shown) clearly showed an additional H-1 resonance (4.467 ppm) from a sugar residue linked in the β-configuration ($^{3}J_{1,2}$=7–9 Hz). This was accompanied by a downfield shift of the β-GlcNAc H-1 resonance to 4.7 19 ppm (Δδ0.065), as expected upon glycosylation of that residue. However, anomeric chemical shift criteria alone are insufficient for determining the identity and linkage position of the newly added residue. Since we were unable to find NMR data for the para-nitrophenyl glycosides of either the Core 3 substrate or the expected Galβ3Core 3 product in the literature or in glycoconjugate NMR databases, and since the substantial anisotropic effects of the paranitrophenyl group obviate direct comparison of chemical shift data with those of the benzylglycosides (Pollex-Kruger, A., Meyer, B., Stuike-Pill, R., Sinnwell, V., Matta, K. L. and Brockhausen, I. Preferred conformations and dynamics of five core structures of mucin type O-glycans determined by NMR spectroscopy and force field calculations. *Glycoconjugate J* 10:365–380, 1993)).

TABLE VII $^{1}$H, $^{13}$C chemical shifts (ppm) and
$^{1}$H—$^{1}$H coupling constants (Hz) for
Core3-p-Nph substrate and biosynthetic
Galβ3-Core3-p-Nph product in D₂O at 25° C.

|  | Core 3 | | Galβ1-3-Core3 | | |
| --- | --- | --- | --- | --- | --- |
|  | GlcNAcB3 | GalNAcα | Galβ3 | GlcNAcβ3 | GalNAcα |
| H-1[a] | 4.654 | 5.785 | 4.467 | 4.719 | 5.787 |
| H-2 | 3.734 | 4.502 | 3.525 | 3.866 | 4.505 |
| H-3 | 3.584 | 4.237 | 3.651 | 3.854 | 4.253 |
| H-4 | 3.488 | 4.291 | 3.919 | 3.589 | 4.303 |
| H-5 | 3.453 | 4.002 | 3.721 | 3.498 | 4.002 |
| H-6R | 3.780 | 3.732 | 3.764 | 3.800 | 3.731 |
| H-6S | 3.918 | 3.679 | 3.764 | 3.918 | 3.681 |
| H-8 (Me) | 2.033 | 2.036 | N.A.[b] | 2.026 | 2.037 |

TABLE VII-continued $^1$H, $^{13}$C chemical shifts (ppm) and
$^1$H—$^1$H coupling constants (Hz) for
Core3-p-Nph substrate and biosynthetic
Galβ3-Core3-p-Nph product in D$_2$O at 25° C.

|  | Core 3 | | Galβ1-3-Core3 | | |
| --- | --- | --- | --- | --- | --- |
|  | GlcNAcβ3 | GalNAcα | Galβ3 | GlcNAcβ3 | GalNAcα |
| $J_{1,2}$ | 8.2 | 3.6 | 8.0 | 8.0 | 3.7 |
| $J_{2,3}$ | 10.2 | 11.3 | 10.3 | N.F.O.$^c$ | 10.9 |
| $J_{3,4}$ | 8.2 | 3.1. | 3.6 | 8.0 | 3.0 |
| $J_{4,5}$ | 9.8 | <1.5 | <1.5 | 10.1 | <1.5 |
| $J_{5,6R}$ | 5.1 | 7.7 | N.D.$^d$ | 5.1 | 8.0 |
| $J_{5,6S}$ | 2.1 | 4.6 | N.D. | 2.2 | 4.4 |
| $J_{6R,6S}$ | −12.3 | −11.8 | N.F.O. | −12.4 | −11.7 |
| C-1 | 102.33 | 95.51 | 103.24 | 101.99 | 95.48 |
| C-2 | 55.38 | 47.80 | 70.41 | 54.45 | 47.76 |
| C-3 | 73.17 | 75.88 | 72.31 | 81.86 | 76.01 |
| C-4 | 69.53 | 68.36 | 68.29 | 68.25 | 68.27 |
| C-5 | 75.48 | 71.63 | 75.10 | 74.94 | 71.61 |
| C-6 | 60.25 | 60.69 | 60.75 | 60.21 | 60.63 |
| C-7 (C=O) | 174.28 | 173.61 | N.A. | N.D. | N.D. |
| C-8 (Me) | 21.99 | 21.76 | N.A. | 21.90 | 21.79 |

$^a$chemical shifts are referenced to internal acetone (2.225 and 30.00 ppm for $^1$H and $^{13}$C, respectively).
$^b$N.A., not applicable.
$^c$N.F.O. non-first-order.
$^d$N.D., not determined.

Analysis of coupling constant data confirmed that the additional residue was a β-Gal ($_3J_{3'4}$<1.5 Hz). The 1→3 linkage was confirmed by the following criteria: (i) the largest glycosylation-induced chemical shift change among the core3 protons was observed for β-GlcNAc H-3 (Δδ= 0.270); (ii) consistent with this, in a $^1$H-$^1$H ROESY spectrum of the product (not shown), the strongest rotating frame Overhauser enhancement observed from β-Gal H-1 was to β-GlcNAc H-3; (iii) no other inter-residue correlations were observed originating from β-Gal H-1, and no ambiguity is introduced into interpretation of the ROESY spectrum by the near degeneracy of β-GlcNAc H-2 and H-3 in the product, since there is no potential glycosylation site at C-2; (iv) comparison of $^{13}$C spectral data for the substrate and product showed only one glycosylation-induced significant downfield shift, for β-GlcNAc C-3 (Δδ8.69). The magnitude of the $^{13}$C shift change is essentially diagnostic for glycosylation at that site.

The product formed with Gb$_4$ was characterized by 1-D $^1$H-NMR spectroscopy (not shown); although more than one component was detected, five anomeric resonances were clearly observed for the major component, with chemical shifts and $^3J_{1,2}$ coupling constants virtually identical to those obtained previously for Galβ1-3Gb$_4$ (Kannagi, R., Levery, S. B., Ishigami, F., et al. New globosides glycosphingolipids in human teratocarcinoma reactive with the monoclonal antibody directed to a developmentally regulated antigen, stage-specific embryonic antigen 3. *J. Biol. Chem.* 258:8934–8942, 1983). These were 4.810 ppm ($^3J_{1,2}$=3.6 Hz), 4.620 ppm ($^3J_{1,2}$=8.7 Hz), 4.267 ppm ($^3J_{12}$=7.4 Hz), 4.198 ppm ($^3J_{1,2}$=7.9 Hz), and 4.173 ppm ($^3J_{1,2}$=7.9 Hz), corresponding to H-1 of Galα4, GalNAcβ3, Galβ4, Galβ3, and Glcβ1, respectively, of the Galβ1→3Gb$_4$ sequence. Anomeric resonances from some unreacted Gb$_4$ were also detected in the product. The identity of a third, minor component, separable by preparative HPTLC, is currently under investigation.

5.6. Northern Analysis of β3GAL-T5

Northern analysis of multiple tissue northern (MTN) blots from Clontech failed to produce signals in several attempts. Sequence analysis suggested that the transcript could exceed 10 kilobase (kb), based on the finding that the first upstream polyadenylation consensus signal. Therefore, an absence of signal on the commercial blots could be explained by poor transfer of large mRNAs. A blot was prepared with total RNA from human carcinoma cell lines, and care was taken to insure efficient transfer of long mRNA species. This yielded hybridizing bands at 12 kb or bigger for three cell lines: AsPC-I, HPAF, Suit2, and S2-013. Interestingly, apart from the single EST identified for the coding region of (β3Gal-T5), no ESTs derived from any part of the 3'UTR of the approximate 10 kb region have been included in the EST databases. It is unclear at this time why this protein of average mass is encoded by a 12 kb mRNA transcript.

5.7. DNA, Vectors, and Host Cells for β3GAL-T5

In practicing the present invention, many conventional techniques in molecular biology, microbiology, recombinant DNA, and immunology, are used. Such techniques are well known and are explained fully in, for example, Sambrook et al., 1989, *Molecular Cloning. A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning;* the series, *Methods in Enzymology* (Academic Press, Inc.); *Gene Transfer Vectors for Mammalian Cells*, 1987 (J. H. Miller and M. P. Carlos eds., Cold Spring Harbor Laboratory); *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I–IV (Weir and Blackwell eds.); Ausubel et al., eds., in the Current Protocols in Molecular Biology series of laboratory technique manuals, © 1987–1997 Current Protocols, © 1994–1997 John Wiley and Sons, Inc.); and Dyson, N.J., 1991, Immobilization of nucleic acids and hybridization analysis, In: Essential Molecular Biology: A Practical Approach, Vol. 2, T. A. Brown, ed., pp. 111–156, IRL Press at Oxford University Press, Oxford, U.K.; each of which is incorporated by reference herein in its entirety).

The invention encompasses isolated nucleic acid fragments comprising all or part of the nucleic acid sequence disclosed herein as set forth in FIG. 1. The fragments are at least about 8 nucleotides in length, preferably at least about 12 nucleotides in length, and preferably at least about 15–20 nucleotides in length. Further, such fragments may be at least about 50, 100, 200, 500, 1000, 2000, 5000, or 10,000 nucleotides in length. The invention further encompasses isolated nucleic acids comprising sequences that are hybridizable under stringency conditions of 2×SSC, 55° C., to the sequence set fourth in FIG. 1; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoranlidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences as set forth in FIG. 1 or sequence-conservative or function-conservative variants thereof, or a complement thereof, and that has been labelled as described above.

The invention also provides nucleic acid vectors comprising the disclosed sequence or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *Saccharomyces cerevisiae, Schizosaccharornyces pombi,* SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced β3Gal-T5 derived peptides and polypeptides.

Advantageously, vectors may also include a transcription regulatory element (i.e., a promoter) operably linked to the β3Gal-T5-coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild-type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use, for example, as probes for the detection of or related organisms and as templates for the recombinant production of peptides or polypeptides. These and other embodiments of the present invention are described in more detail below.

5.8. Polypeptides of β3GAL-T5

The present invention encompasses isolated peptides (generally defined as a polypeptide having less than 50 amino acid residues) and polypeptides encoded by the disclosed nucleic acid sequence. Peptides are preferably at least five residues in length. Peptides or polypeptides may be, for example, 6, 10, 15, 30, 50, 100, 200, or 300 residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of Matteucci et al., 1981, *J. Am. Chem. Soc.* 103:3185, the method of Yoo et al., 1989, *J. Bid. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well-known in the art, including, without limitation, preparative disc-gel elctrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

5.9. Antibodies of β3GAL-T5

The present invention encompasses various antibodies that specifically recognize immunogenic components derived from β3Gal-T5. Such antibodies can be used, for example, as reagents for detection and purification of β3Gal-T5.

β3Gal-T5 specific antibodies according to the present invention include polyclonal, monoclonal and humanized antibodies, as well as fragments and derivatives thereof. The antibodies of the invention may be elicited in an animal host by immunization with β3 Gal-T5 components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, antibodies may be constructed by biochemical reconstitution of purified heavy and light chains. Antibodies of the invention include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies, single chain antibodies, anti-idiotypic (anti-Id) antibodies, and epitope-binding antibody fragments. Methods for the production of all of the above types of antibodies and derivatives are well-known in the art. For exanple, techniques for producing and processing polyclonal antisera are disclosed in Mayer and Walker, 1987, *Immunochemical Methods in Cell and Molecular Biology*, (Academic Press, London). Further description of the polyclonal, monoclonal, chimeric and humanized antibodies of the invention is set forth below.

Polyclonal antibodies of the invention are heterogeneous populations of antibody molecules derived from the sera of immunized animals. Various procedures well known in the art may be used for the production of polyclonal antibodies to β3Gal-T5 and fragments thereof. For the production of polyclonal antibodies, various host animals can be immunized by injection with β3Gal-T5 or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies of the invention are homogeneous populations of antibodies to a particular antigen. A monoclonal antibody (mAb) to β3Gal-T5 or a fragment or derivative thereof can be prepared by using any technique known in the art which provides for the production of antibody molecules by continuous cell lines in culture. These include but are not limited to the hybridoma technique originally described by Kohler and Milstein (1975, Nature 256, 495–497), and the more recent human B cell hybridoma technique (Kozbor et al., 1983, Immunology Today 4, 72), and the EBV-hybridoma technique (Cole et al., 1985, *Monoclonal Antibodies and Cancer Therapy*, Alan R. Liss, Inc., pp. 77–96). Such antibodies may be of any immunoglobulin class including IgG, IgM, IgE, IgA, IgD and any subclass thereof. The hybridoma producing the mAbs of use in this invention may be cultivated in vitro or in vivo.

Monoclonal antibodies of the invention include but are not limited to human monoclonal antibodies. Human monoclonal antibodies may be made by any of numerous techniques known in the art (e.g., Teng et al., 1983, *Proc. Nat'l Acad. Sci. U.S.A.* 80, 7308–7312; Kozbor et al., 1983, *Immunology Today* 4, 72–79; Olsson et al., 1982, *Meth. Enzymol.* 92, 3–16).

This invention provides chimeric antibodies specific for β3Gal-T5 or a fragment or derivative thereof. A chimeric antibody is a molecule in which different portions are derived from different animal species, such as those having a variable region derived from a murine mAb and a human immunoglobulin constant region. Various techniques are available for the production of such chimeric antibodies (see, e.g., Morrison et al., 1984, *Proc. Nat'l Acad. Sci. U.S.A.* 81, 6851–6855; Neuberger et al., 1984, Nature, 312, 604–608; Takeda et al., 1985, *Nature,* 314, 452–454) by splicing the genes from a mouse antibody molecule of appropriate antigen specificity together with genes from a human antibody molecule of appropriate biological activity.

This invention provides humanized antibodies specific for β3Gal-T5 or a fragment or derivative thereof. Briefly, humanized antibodies are antibody molecules from non-human species having one or more complementarily determining regions (CDRs) from the non-human species and a framework region from a human immunoglobulin molecule. Various techniques have been developed for the production of humanized antibodies (see, e.g., Queen, U.S. Pat. No. 5,585,089, which is incorporated herein by reference in its entirety). An immunoglobulin light or heavy chain variable region consists of a "framework" region interrupted by three hypervariable regions, referred to as complementarily determining regions (CDRs). The extent of the framework region and CDRs have been precisely defined (see, Kabat et al., 1983, Sequences of proteins of immunological interest, U.S. Department of Health and Human Services).

Further, techniques described for the production of single chain antibodies (U.S. Pat. No. 4,946,778; Bird, 1988, *Science* 242, 423–426; Huston et al., 1988, *Proc. Nat'l. Acad. Sci. U.S.A.* 85, 5879–5883; and Ward et al., 1989, *Nature* 334, 544–546) can be adapted to produce single chain antibodies specific for β3Gal-T5 or a fragment or derivative thereof. Single chain antibodies are formed by linking the heavy and light chain fragments of the Fv region together via an amino acid bridge, resulting in a single chain polypeptide.

Antibody fragments which recognize specific epitopes of β3Gal-T5 or a fragment or derivative thereof may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science*, 246, 1275–1281) to allow rapid and easy identification of monoclonal Fab fragments with the desired specificity.

Further, general methods of antibody production and use are suitable for the antibodies of the invention. For example see Harlow and Lane, 1988, *Antibodies: A Laboratory Manual*, Cold Spring Harbor Laboratory Press, Cold Spring Harbor, N.Y., which is incorporated herein by reference in its entirety.

The antibodies of the invention can be purified by standard methods, including but not limited to preparative disc-gel electrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification*, 1989, Amicon Division, W. R. Grace & Co. General protein purification methods are described in *Protein Purification: Principles and Practice*, R. K. Scopes, Ed., 1987, Springer-Verlag, New York, N.Y.

Anti-β3Gal-T5 antibodies, whether unlabeled or labeled by standard methods, can be used as the basis for immunoassays. The particular label used will depend upon the type of immunoassay used. Examples of labels that can be used include, but are not limited to, radiolabels such as $^{32}$P, $^{125}$I, $^{3}$H and $^{14}$C; fluorescent labels such as fluorescein and its derivatives, rhodamine and its derivatives, dansyl and umbelliferone; chemiluminescers such as luciferia and 2,3-dihydrophthal-azinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described in, e.g., Chan (Ed.), 1987, *Immunoasscry: A Practical Guide*, Academic Press, Inc., Orlando, Fla.

The invention described and claimed herein can be further appreciated by one skilled in the art through reference to the examples which follow. These examples are provided merely to illustrate several aspects of the invention and shall not be construed to limit the invention in any way.

6. EXAMPLES

Using BLAST analysis of an EST database, we identified a total of ten candidate human homologous members of the β3Gal-T gene family including the four members previously reported (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998). Analysis of sequence similarity of the first four members revealed features indicative of functions of encoded enzymes, including conservation of cysteine residues, spacing of conserved motifs, and hydropathy profiles (Amado, M., Almeida, R., Carneiro, F., et al. A family of human β3-galactosyltransferases: characterisation of four members of a UDP-galactose β-N-acetylglucosamine/β-N-acetylgalactosamine β1,3-Galactosyltransferase family. *J. Biol. Chem.* 273:12770–12778, 1998). β3Gal-T4 differed significantly from β3Gal-T1, -T2, and -T3 in this respect, and the function of this enzyme was different in that the acceptor saccharide was βGalNAc in ganglioseries glycolipids (Miyaki, H., Fukumoto, S., Okada, M., Hasegawa, T. and Furukawa, K. Expression cloning of rat cDNA encoding UDP-galactose G(D2) β1,3 galactosyltransferase that determines the expression of G(D1 b)/G(M 1)G(A1). *J. Biol. Chem.* 272:24794–24799, 1997; Amado, M., Almeida, R., Cameiro, F., et al. A family of human β3-galactosyltransferases: characterisation of four members of a UDP-galactose β-N-acetylglucosamnine/β-N-acetylgalactosamine β1,3-Galactosyltransferase family. *J. Biol. Chem.* 273:12770–12778, 1998).

A sequence derived from an EST clone (GenBank accession number AJ003597) was predicted to represent a new gene encoding a β3Gal-T forming the Galβ1-3GlcNAc linkages. This report describes the cloning and expression of this gene, designated p3Gal-T5, and demonstrates that the encoded enzyme has better kinetic properties than those of the previously cloned β3Gal-Ts. β3Gal-T5 is a candidate for the β3Gal-T activity found in epithelia.

6.1. Identification and Cloning of β3Gal-T5

The BLASTn and tBLASTn were used with the coding sequence of human β3Gal-T2 to search the dbEST database at The National Centre for Biotechnology Information (NCBI, USA) as previously described (Almeida, R., Amado, M., David, L., et al. A Family of Human β4-Galactosyltransferases: Cloning and expression of two novel UDP-GalactOSe β-N-Acetylglucosaflhine ⊖1,4-GalactosyltransferaSes, β4Gal-T2 and β4Gal-T3. *J.Biol.Chem.* 272:31979–31992, 1997). One EST (GenBank accession number AJ003597) was identified as representing a putative novel β3Gal-T gene. Since the coding regions of all other cloned members of the human β3Gal-T gene family were found to be encoded in a single exon, we used the EST sequence information to design primers for PCR screening of a P1 genomic library. A human foreskin P1 library (DuPont Merck Pharmaceutical Company Human Foreskin Fibroblast P1 Library) was screened using the primer pairs EBER 1301 (5'-CTTCCTTAAGCTCCCAGATAC 3') (SEQ ID NO:1) and EBER 1302 (5'-GTTTCCGCTGCACTGCTGGTG 3') (SEQ ID NO:2). One β1 clone for β3Gal-T5 (DMPC-HFF#1-1195h3) as well as DNA from P1 phages were obtained from Genome Systems Inc. Sequencing of this P1 DNA revealed an open reading frame of 933 bp encoding a putative protein with a type II domain structure (FIG. 1). The entire coding sequence of β3Gal-T5 was filly sequenced using automated sequencing (ABI377, Perkin Elmer) with dye terminator chemistry. The EST clone AJ003597 was derived from a chromosome 21 library, and subsequently a 165 kilobase pair PAC sequence containing the entire sequence of β3Gal-T5 was linked to 21 q22.3 (GenBank accession number-AF064860). The EST sequence did not appear to be derived from correct oligo-dT priming, and analysis of the genomic PAC sequence showed that the first downstream consensus polyadenylation signal (AATAAA) was 9568 bp from the first initiation codon. The putative 3' UTR sequence contained repeats and potential short coding regions, but none of the coding regions showed similarity to known genes. No ESTs from the 3'UTR have been deposited in the GenBank database. A second consensus polyadenylation signal is found 2991 bp downstream of the first, and a few 3' ESTs have been identified from this site and mapped (STS-N41029), but no sequence encoding protein with similarity to known genes have been assigned from this region.

The EST sequence (AJ003597) is 338 nucleotides long. Nucleotides 1–312 of AJ003597 encode the complement of nucleotides 38–349 of the coding region of β3Gal-T5 (FIG. 1) (nucleotides 116–427 of SEQ ID NO:8).

6.2. Expression of β3Gal-T5

What follows are examples of expression of β3Gal-T5 in insect cells, and as a full-length or partial-length (soluble) gene product in CHO cells.

6.2.1. Expression of β3Gal-T5 in Insect Cells

An expression construct (pAcGP67-β3Gal-T5-sol) designed to exclude the hydrophobic transmembrane segment and to encode amino acid residues 25–310, was prepared by PCR using P1 genomic DNA, and the primer pair EBER1300 sol (5'-ATGTACAGTCTAAATCCTTTC) (SEQ ID NO:3) and EBER1310 (5'-TCAGACAGGCGGACAATCTTC) (SEQ ID NO:4) (FIG. 1), which included BamHI restriction sites. PCR product was cloned into the BamHI site of pAcGP67B (Pharmingen). An expression construct (pVL-β3Gal-T5-full) designed to encode the full coding sequence (from first ATG, FIG. 1) was prepared by PCR with P1 genomic DNA using the primer pair EBER1309 (5'-ATGGCTTCCCGAAGATGAG) (SEQ ID NO:5) and EBER1310. This PCR product was cloned into the BamHI site of pVL1193 (Pharmingen). Both soluble and full length constructs were fully sequenced to confirm fidelity. Plasmids pAcGP67-β3GalT5-sol and pVL-β3Gal-T5-full were co-transfected with Baculo-Gold™ DNA (Pharmingen) as described previously (Bennett, E. P., Hassan, H. and Clausen, H. cDNA cloning and expression of a novel human UDP-N-acetyl-alpha-D-galactosamine. Polypeptide N-acetyl-galactosaminyl-transferase, Gal NAc-T3. *J. Biol. Chem.* 271:17006–17012, 1996). Recombinant Baculo-virus were obtained after two successive amplifications in Sf9 cells grown in serum-containing medium, and titers of virus were estimated by titration in 24-well plates with monitoring of enzyme activities. Controls included pAcGP67-β3Gal-T1 (Amado, M., Almeida, R., Cameiro, F., et al. A family of human β3-galactosyltransferases: characterization of four members of a UDP-galactose β-N-acetylglucosamine/β-N-acetylgalactosamine β1,3-Galactosyltransferase family. *J. Biol. Chem.* 273:12770–12778, 1998), pAcGP67-β3Gal-T2 (Id.), pAcGP67-β4Gal-T2 (Almeida, R., Amado, M., David, L., et al. A Family of Human β4-Galactosyltransferases: Cloning and expression of two novel UDP-Galactose β-N-Acetylglucosamine β1,4-Galactosyltransferases, β4Gal-T2 and β4Gal-T3. *J.Biol.Chem.* 272:31979–31992, 1997), pAcGP67-β4Gal-T3 (Id.), and pAcGP67-GalNAc-T3-sol (Bennett, E. P., Hassan, H. and Clausen, H. cDNA cloning and expression of a novel human UDP-N-acetyl-alpha-D-galactosamine. Polypeptide N-acetyl-galactosaminyl-transferase, GafNAc-T3. *J. Biol. Chem.* 271:17006–17012, 1996). For large scale expression amplified virus was used to infect High Five™ cells grown in serum-free media (Invitrogen) in upright roller bottles shaking at 140 rpm and 27° C.

The kinetic properties were determined with partially purified, secreted forms of the enzymes. Semipurification of enzymes from serum-free medium of infected High-Five™ cells was performed by sequential Amberlite, DEAE-Sephacel and 5-Sepharose chromatography as described previously (Wandall, H. H., Hassan, H., Mirgorodskaya, E., et al. Substrate specificities of three members of the human UDP-N-acetyl-alpha-D-galactosamine:Polypeptide Nacetylgalactosaminyltransferase family, GalNAc-T1, -T2, and -T3. *J. Biol. Chem.* 272:23503–235 14, 1997). Comparisons of enzymes were performed relatively to the activity obtained with β3GlcNAc-Bzl (Tables II and III). Full length enzymes were assayed with 1% Triton CF54 homogenates of washed cells. Enzyme assays were performed in 50 μl total reaction mixtures containing 25 mM Cacodylate (pH 7.5), 10 mM MnCl$_2$, 0.25% Triton X-100, 100 μM UDP-[$^{14}$C]-Gal (2,600 cpm/nmol) (Amersham), and varying concentrations of acceptor substrates (Sigma) (see Table I for structures). Reaction products were quantified by Dowex-1 chromatography. Assays with glycoproteins were performed with the standard reaction mixture modified to contain 150 μM UDP-Gal, 54 mM NaCl, and 0.5 mg ovalbumin, asialo-agalacto-fetuin, orosomucoid, or bovine submaxillary mucin acceptor substrates obtained as previously described (Schwientek, T., Almeida, R., Levery, S. B., Holmes, E., Bennett, E. P. and Clausen, H. Cloning of a novel member of the UDP-galactose: β-N-acetylglucosamine β1,4-galactosyltransferase family, β4Gal-T4, involved in glycosphingolipid biosynthesis. *J. Biol. Chem.* 273:29295–29305, 1998). The transfer of Gal was evaluated after acid precipitation by filtration through Whatman GF/C glass fibre filters. Assays to determine Km of acceptor substrates and donor substrates were modified to include 200 μM UDP-[$^{14}$C]-Gal (2,600 cpm/nmol) or 30 mM GlcNAcβ-benzyl. Assays with glycolipid acceptors were conducted as previously described (Holmes, E. H. Characterization and membrane organization of beta 1-3- and beta 1-4-galactosyltransferases from human colonic adenocarcinoma cell lines Cob 205 and SW403: basis for preferential synthesis of type 1 chain lacto-series carbohydrate structures. *Arch Biochem Biophys* 270:630–646, 1989) in reaction mixtures containing 2.5 μmol HEPES buffer, pH 7.2, μmol MnCl$_2$, 100 μg taurodeoxycholate or Triton CF-54, 20 μg acceptor glycolipid, 15 nmol UDP-[$^{14}$C]-galactose (13,000 cpm/nmol) and enzyme in a total volume of 100 µl. Conditions for incubation and product isolation were as previously described (Id.).

6.2.2. Stable Expression of Full Coding Sequence of β3Gal-T5 inN CHO Cells

A cDNA sequence encoding the full coding sequence of the β3Gal-T5 gene was derived by RT-PCR using primers EBER 1309 and EBER 1310 with BamHI restriction sites introduced. The PCR product was designed to yield a β3Gal-T5 protein with a hydrophobic transmembrane retention signal in order to have the enzyme expressed and positioned in the appropriate Golgi compartment of the transfected cell. The PCR product was inserted into the BamHI site of a mammalian expression vector pCDNA3 (Invitrogen), and the construct, pCDNA3-β3Gal-T5-mem, was transfected into CHO cells and stable transfectants were selected. Further details are provided below.

The full-length Golgi-retained form of β3Gal-T5 was stably expressed in Chinese Hamster Ovary cells (CHO-K1) obtained from ATCC. The full-length coding construct, designed to contain amino acids 1–310, was prepared by PCR with P1 genomic DNA using the primer pair EBER1309 and EBER 1310 (FIG. 1), which included BamHI restriction sites. Correct insertion of the PCR product cloned into the BamHI site of the pcDNA3 vector (Invitrogen) was confirmed by sequencing. The predicted coding region of the construct is shown in FIG. 1. CHO-K1 cells were transfected using 0.2 µg DNA and 5 µg lipofectamine (Invitrogen) in subconfluent 6 well plates according to the manufacturer's protocol. After 48 hours, the medium was changed and 400 µg/ml G418 was added. At 72 hours 10–20% of the wells were trypsinized and the percentage of cells expressing β3Gal-T5 was evaluated by immunocytology using an anti-β3Gal-T5 monoclonal antibody, UH9.

6.2.3. Stable Expression of Soluble Form of β3Gal-T5 in CHO Cells cDNA pAcGP67-β3Gal-T5-sol containing the coding sequence of a soluble, secreted β3Gal-T5 enzyme was cloned into the BamHI site of a modified mammalian expression vector, pCDNA3 (Invitrogen). pcDNA3 was modified by insertion of an interferon signal peptide sequence into the KpnI/BamHI site of ensuring secretion of the expressed product when cloned into the vector. The pcDNA3-γINF-β3Gal-T5-sol construct was transfected into CHO cells and stable transfectants were selected. Further details are provided below.

The secretable form of β3Gal-T5 was stably expressed in Chinese Hamster Ovary cells (CHO-K1) obtained from ATCC. A truncated construct, designed to contain amino acids 25–310, was prepared by PCR using P1 genomic DNA and the primer pair EBER1300 sol (SEQ ID NO:3) and EBER1310 (SEQ ID NO:4) (FIG. 1), which included BamHI restriction sites. The PCR product was cloned into the BamHI site of a modified pcDNA3 vector (Invitrogen). The pcDNA3 vector was modified to include 19 amino acids of the gamma-interferon signal sequence by directional insertion of a synthetic sequence of 91 bp coding for the interferon sequence with KpnI and BamHI flanking sites. The modified pcDNA3 vector was constructed as follows. Four synthetic oligonucleotides were synthesized: INFFOR (5'-cggggtaccggaaacgatgaaatatacaag-3') (SEQ ID NO:14); INFREVA (5'-ggcggatccaggcagatcacagccaagagaacccaaaacg-3') (SEQ ID NO:15); INFREVB (5'-gcggatcccaggcagatcacagccaagagaacccaaaacg-3') (SEQ ID NO:16); and INFREVC (5'-gcggatccccaggcagatcacagccaagagaacccaaaacg3') (SEQ ID NO:17). Oligonucleotide primer pairs INFFOR/INFREVA, INFFOR/INFREVB and INFFOR/INFREVC were used to PCR amplify an interferon coding DNA fragment from human genomic DNA under the following conditions: 95° C. for 30 seconds, 60° C. for 5 seconds, 72° C. for 15 seconds, using Ampli-Taq (Perkin-Elmer Cetus) and a model 480 Thermocycler (Perkin-Elmer). The use of three 3' primers spaced one base apart yields three vectors with a BamHI site positioned for any of three reading frames with respect to the signal sequence.

CHO-K1 cells (ATCC) were transfected using 0.2 µg DNA and 5 µg lipofectamine (Invitrogen) in subconfluent 6 well plates according to the manufacturer's protocol. After 48 hours, the medium was changed and 400 µg/ml G418 was added. At 72 hours 10–20% of the wells were trypsinized and the percentage of cells expressing β3Gal-T5 was evaluated by immunocytology using an anti-p3Gal-T5 monoclonal antibody, UH9.

6.3. Characterization of the Profuct Formed with Core3-p-Nph by β3Gal-T5

Complete glycosylation of core3-p-Nph was performned in a reaction mixture consisting of 1 mU β3Gal-T5 (specific activity determined with βGlcNAc-Umb), 2 mg core3-p-Nph, 50 mM Tris (pH 7.0), 1 mM $MnCl_2$, 0.01% Triton X-100, and 4.6 µmol UDP-Gal in a final volume of 500 µl. The glycosylation was monitored by HPTLC and was complete after 3 hours incubation. The reaction product was isolated as previously described on octadecyl-silica cartridges ("Bakerbond;" J. T. Baker, Phillipsburg, N.J.) (Almeida, R., Amado, M., David, L., et al. A Family of Human β4-Galactosyltransferases: Cloning and expression of two novel UDP-Galactose β-N-Acetylglucosamine β1,4-Galactosyltransferases, β4Gal-T2 and β4Gal-T3. J.Biol. Chem. 272:31979–31992, 1997) using successive stepwise elutions with MeOH. The MeOH solution was evaporated to dryness and subjected to $^1$H-NMR analysis as described below.

6.3.1. 1-D $^1$H-NMR Spectrpsocpy of Rraction Products with Core3-p-Nph and $Gb_4$ The purified product from reaction with core3-p-NPh was deuterium exchanged by repeated sonication and lyophilization from $D_2O$. A saturated solution in $D_2O$ was used for NMR analysis. 1-D $^1$H-NMR, 2-D $^1$H-$^1$H-TOCSY (Braunschweiler, L. and Ernst, R. R. Coherence transfer by isotropic mixing: Application to proton correlation spectroscopy. J. Magn. Reson. 53:521–528, 1983; Bax, A. and Davis, D. G. MLEV-1 7-based two-dimensional homonuclear magnetization transfer spectroscopy. J. Magn. Reson. 65:355–360, 1985a) and -ROESY (Bothner-By, A. A., Stephens, R. L., Lee, J. M., Warren, C. D. and Jeanloz, R. W. Structure determination of a tetrasaccharide: Transient nuclear Overhauser effects in the rotating frame. J.Am. Chem. Soc 106:811–813, 1984; Bax, A. and Davis, D. G. Practical aspects of two-dimensional transverse NOE spectroscopy. J. Magn. Reson. 63:207–213, 1985b) experiments were performed at 298° C. on a Varian Unity Inova 600 MHz spectrometer (0.5 mL in 5 mm tube) using standard acquisition software available in the Varian VNMR software package. A $^1$H-detected, $^{13}$C-decoupled, phase sensitive, gradient (Davis, A. L., Keeler, J., Laue, E. D. and Moskau, D. Experiments for recording pure-absorption heteronuclear correlation spectra using pulsed field gradients. *J. Magn. Reson.* 98:207–216, 1992) $^{13}$C-$^{1}$H-HSQC (Bodenhausen, G. and Ruben, D. J. Natural abundance nitrogen-15 NMR by enhanced heteronuclear spectroscopy. *Chem. Phys. Lett.* 69:185–189, 1980) experiment was performed at 298° C. on a Varian Unity Inova wide bore 500 MHz spectrometer (2 mL in 8 mm tube). A 2 mg sample of core3-pNph was prepared in similar fashion and analyzed under identical conditions for comparison. Chemical shifts are referenced to internal acetone (2.225 and 29.92 ppm for $^{1}$H and $^{13}$C, respectively).

The purified glycosphingolipid products from reaction with Gb$_4$ were deuterium exchanged by dissolving in CDCl$_3$-CD,OD 2:1, evaporating thoroughly under dry nitrogen (repeating 2×), and then dissolved in 0.5 mL DMSO-d$_6$/2% D$_2$O (Dabrowski, J., Hanfland, P. and Egge, H. Structural analysis of glycosphingolipids by high resolution 1H nuclear magnetic resonance spectroscopy. *Biochemistry* 19:5652–5658, 1980) for NMR analysis. 1-D $^{1}$H-NMR spectra were acquired at 600 MHz (temperature, 308° K); 10,000 FIDs were accumulated, with solvent suppression by presaturation pulse during the relaxation delay. Spectra were interpreted by comparison to spectra of relevant glycosphingolipid standards acquired previously under comparable conditions (Dabrowski, J., Hanfland, P. and Egge, H. Structural analysis of glycosphingolipids by high resolution 1H nuclear magnetic resonance spectroscopy. *Biochemistry* 19:5652–5658, 1980; Kannagi, R., Levery, S. B., Ishigami, F., et al. New globosides glycosphingolipids in human teratocarcinoma reactive with the monoclonal antibody directed to a developmentally regulated antigen, stage-specific embryonic antigen 3. *J. Biol. Chem.* 258:8934–8942, 1983).

6.4. Restricted Organ Expression Pattern of β3Gal-T5

Total RNA was isolated from human adenocarcinoma cell lines AsPC-1, BxPC-3, Capan-1, Capan-2, Colo357, HPAF, HT-29, PANC-1, Suit2, and S2-013 as described previously (Sutherlin, M. E., Nishimori, I., Caffrey, T., et al. Expression of three UDP-N-acetyl-alpha-D galactosamine:polypeptide GalNAc N-acetylgalactosaminyl-transferases in adenocarcinoma cell lines. *Cancer Res* 57:4744–4748, 1997). Twenty five μg of total RNA was subjected to electrophoresis on a 1% denaturing agarose gel and transferred to nitrocellulose as described previously (Sutherlin, M. E., Nishimori, I., Caffrey, T., et al. Expression of three UDP-N-acetyl-alpha-D galactosamine:polypeptide GalNAc N-acetylgalactosaminyltransferases in adenocarcinoma cell lines. *Cancer Res* 57:4744–4748, 1997). Human Multiple Tissue northern blots, MTNI and MTNII, were obtained from Clontech. The soluble expression construct was used as probe. The probe was labeled by random priming using αP$^{32}$dCTP (Amersham) and an oligo labeling kit (Pharmacia). The blots were probed overnight at 42° C. as previously described (Bennett, E. P., Hassan, H. and Clausen, H. cDNA cloning and expression of a novel human UDP-N-acetyl-alpha-D-galactosamine. Polypeptide N-acetyl-galactosaminyl-transferase, GalNAc-T3. *J. Biol. Chem.* 271:17006–17012,1996), washed 2×10 min at RT with 2×SSC, 1% Na$_4$P$_2$O$_2$, 2×20 min at 65° C. with 0.2× SSC, 1% SDS, 1% Na$_4$P$_2$O$_2$ and once 10 min with 0.2×SSC at RT ("preferred hybridization conditions").

6.5. Analysis of DNA Polymorphism of the β3Gal-T5 Gene

Primer pairs EBER 1320 (5'-CAGCGAGGTTCTAGAGTTTCC-3') (SEQ ID NO:6) and EBER 1321 (5'-GAAATCCACGCCAGAATGTCG-3') (SEQ ID NO:7) for amplification of the entire coding sequence have been used for PCR amplification of exon 1. The PCR product was subcloned and the sequence of 10 clones containing the appropriate insert was determined assuring that both alleles of each individual are characterized.

6.6. Antibodies to β3Gal-T5

An anti-β3Gal-T5 monoclonal antibody, UH9, was prepared by immunizing mice with a purified β3Gal-T5 preparation that gave a single band of approximately 35,000 on SDS-PAGE Coomassie stained gel. Balb/c mice were immunized with one subcutaneous or intraperitoneal injection of 10 μl undematured protein in Freunds complete adjuvant, followed by two injections with Freunds incomplete adjuvant, and finally an intravenous booster without adjuvant. Eyebleeds were taken 7 days after third immunization, and the titer and specificity of anti-β3Gal-T5 antibodies was evaluated. Fusion to NS-1 and the cloning procedure was as described in White et al., Biochemistry 29:2740 (1990). The mononclonal antibody UH9 was selected for reactivity with unfixed cells and/or tissues, as well as ability to immunoprecipitate β3Gal-T5 activity. Hybridomas were selected by three criteria: (i) differential reactivity in ELISA assays with purified recombinant enzymes; (ii) immunocytology on Sf9 cells two days after infection with Baculovirus containing β3Gal-transferases, β3Gal-T1, -T2, -T3, -T4, and -T5; and (iii) differential immunoprecipitation of active recombinant enzymes.

ELISA analysis was performed as described by White et al. (Id.), using purified recombinant β3Gal-T1, -T2, and -T5, using an initial antigen concentration of 10 μg/ml.

The inmuunocytology assay was performed by washing trypsinized cells twice in PBS and air drying the washed cells onto coverslides. Dried slides were fixed in 1 00% ice cold acetone for 10 min, dried, and incubated with monoclonal anti-β3Gal-T5 antibody for 1 hour. After washing with PBS, slides were incubated with FITC-conjugated rabbit anti-mouse IG for 30 minutes, washed with PBS and mounted in glycerol and analyzed by microscopy.

Immunoprecipitation of recombinant human β3Gal-transferases was performed as follows. Secreted forms of human β3Gal-transferases were expressed in Sf9 cells and media were harvested three days post-infection and used as enzyme source. Protein G Sepharose was saturated sequentially with rabbit anti-mouse IgG and monoclonal antibodies as culture supernatants. A 5% suspension of Protein G beads was added to Sf9 medium containing either GalNAc-T1, -T2, -T3 or -T4. After incubation for 1 hour at 4 degrees C., beads were washed in PBS, and resuspended in 25 mM Tris (pH 7.4), 0.25% Triton X-100. β3Gal-transferase activities were measured in the supematants and the washed pellets. UH9 selectively inmmunoprecipitated β3Gal-T5 activity but not β3Gal-T1 or -T2 activity.

Western blot analysis with purified recombinant enzymes was also performed. It proved difficult to select antibodies reactive with both the native and the denatured β3Gal-T5 enzyme. The antibody UH9 is therefore likely to be directed to a conformational epitope, and to detect the native conformation of β3Gal-T5. Another antibody, designated UH10, only reacted with denatured β3Gal-T5 as evidenced by ability to western blot. This antibody did stain insect cells infected with pVL-β3Gal-T5-full and pAcGP67-β3Gal-T5-sol, but it did not stain CHO cells stably transfected with the β3Gal-T5 expression constructs or various epithelial cell lines and tissues. Furthermore, UH10 did not immunoprecipitate 3Gal-T5 enzyme activity.

To correlate immunoreactivity with enzyme activity, transfected cells expressing soluble β3Gal-T5 were trypsinized and plated in 96 well plates. Two rounds of screening and cloning by limiting dilution using immunoreactivity with UH9 were performed and clones achieving over 50% positive cells were selected and tested for level of secreted enzyme in supernatant of confluent cultures. The intensity of immunoreactivity by the cytology assay correlated in all cases with level of β3Gal-T5 enzyme activity found in spent media from clones.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety.

What is claimed is:

1. An isolated nucleic acid of less than 10,000 nucleotides or a complement thereof comprising a nucleotide sequence encoding UDP-galactose: β-N-acetylglucosamine β1,3galactosyltransferase (β3Gal-T5), as set forth in SEQ ID NO:9.

2. The isolated nucleic acid of claim 1 which is DNA.

3. The isolated DNA of claim 2 which is cDNA or genomic DNA.

4. The isolated nucleic acid of claim 1 which is RNA.

5. An isolated nucleic acid of less than 10,000 nucleotides or a complement thereof comprising nucleotides 151–1008 of SEQ ID NO:8.

6. An isolated nucleic acid of less than 10,000 nucleotides or a complement thereof comprising the nucleotide sequence set forth in SEQ ID NO:8.

7. A nucleic acid vector of less than 50,000 nucleotides comprising an isolated nucleotide sequence encoding a polypeptide comprising the polypeptide set forth in SEQ ID NO:9.

8. A nucleic acid vector of less than 10,000 nucleotides comprising an isolated nucleotide sequence encoding a polypeptide comprising the polypeptide set forth in SEQ ID NO:9.

9. The vector of claim 8, wherein nucleotide sequence is operably linked to a transcriptional regulatory element.

10. A nucleic acid vector of less than 50,000 nucleotides comprising the nucleotide sequence of claim 5.

11. A host cell comprising the nucleic acid vector of claim 8.

12. A host cell stably transfected with the nucleic acid vector of claim 9.

13. The host cell of claim 11, wherein the nucleic acid vector is stably transfected.

14. The host cell of claim 11 which produces β3Gal-T5 enzymatic activity.

15. The host cell of claim 11 which is selected from the group consisting of a bacterial cell, a yeast cell, an insect cell, an avian cell and a mammalian cell.

16. The host cell of claim 14 which is selected from the group consisting yeast cell, an insect cell, an avian cell and a mammalian cell.

17. The insect cell of claim 16 which is a *Spodoptera frugiperda* cell.

18. The mammalian cell of claim 16 which is a chinese hamster ovary cell.

19. A host cell comprising the nucleic acid vector of claim 10.

20. A method for producing a polypeptide comprising a β3Gal-T5 polypeptide as set forth in SEQ ID NO:9, which comprises:

(i) introducing into a host cell a nucleic acid encoding said β3Gal-T5 polypeptide;

(ii) growing the host cell under conditions suitable for expression of the nucleic acid introduced; and (iii) isolating the β3Gal-T5 polypeptide expressed by the host cell.

21. An isolated β3Gal-T5 polypeptide comprising the amino acid sequence set forth in SEQ ID NO:9.

22. An isolated β3Gal-T5 polypeptide consisting of the amino acid sequence as set forth in SEQ ID NO:9.

23. A polypeptide of claim 21 which displays functional activity of the β3Gal-T5 polypeptide.

24. A polypeptide of claim 21 which is capable of immunospecific binding to an antibody raised against a β3Gal-T5 polypeptide.

25. A fusion protein comprising a polypeptide of claim 24 fused by a covalent bond to an amino acid sequence of a second protein, which second protein is not a β3Gal-T5 polypeptide.

26. An isolated galactosyltransferase polypeptide of claim 25 capable of transferring galactose through a β1-3 linkage to an acceptor substrate selected from the group consisting of GalNAcβ1-3Galα1-4Galβ1-4Glcβ1-Cer, Glcβ1-Cer, GalNAcβ1-4Galβ1-4Glcβ1-Cer, GlcNAcβ1-3Galβ1-4C11cβ1-Cer, and GlcNAcβ1-3Galβ1-4GlcNAcβ1-3Galβ1-4Glcβ1-Cer.

27. An isolated β3Gal-T5 polypeptide as set forth in SEQ ID NO:9, which is capable of transferring galocotose through a β1-3 linkage to GalNAcβ1-3Galα1-4Galβ1-4Glcβ1-Cer.

28. An isolated β3Gal-T5 polypeptide as set forth in SEQ ID NO:9 capable of transferring galactose through a β1-3 linkage to an acceptor substrate selected from the group consisting of a glycoprotein or a glycolipid.

29. The isolated polypeptide or fragment of claim 28, wherein the glycolipid is a glycosphingolipid containing a carbohydrate sequence selected from the group consisting of GlcNAcβ1-6Gal, GlcNAcβ1-6GalNAc, GlcNAcβ1-3GalNAc, GlcNAcβ1-2Man, GlcNAcβ1-4Man, GlcNAcβ1-6Man, GlcNAcβ1-3Man, GlcNAcβ1-ceramide and GalNAcβ1-3Gal.

* * * * *

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 1
cttccttaag ctcccagata c                                              21

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 2
gtttccgctg cactgcactg ctggtg                                         26

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 3
atgtacagtc taaatccttt c                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 4
tcagacaggc ggacaatctt c                                              21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 5
atggctcccg aagatgag                                                  18
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 6
cagcgaggtt ctagagtttc c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 7
gaaatccacg ccagaatgtc g                                              21

<210> SEQ ID NO 8
<211> LENGTH: 1011
<212> TYPE: DNA
<213> ORGANISM: Homo sapiens
<220> FEATURE:
<221> NAME/KEY: CDS
<222> LOCATION: (79)..(1008)

<400> SEQUENCE: 8

```
ccacctcagc ctcctagcat aaaactagac acatcctcat gcttttgagg tctaatcatt       60 ggatttttgtt cctttcag atg gct ttc ccg aag atg aga ttg atg tat atc      111
                    Met Ala Phe Pro Lys Met Arg Leu Met Tyr Ile
                     1               5                  10 tgc ctt ctg gtt ctg ggg gct ctt tgt ttg tat ttt agc atg tac agt       159
Cys Leu Leu Val Leu Gly Ala Leu Cys Leu Tyr Phe Ser Met Tyr Ser
         15                  20                  25 cta aat cct ttc aaa gaa cag tcc ttt gtt tac aag aaa gac ggg aac       207
Leu Asn Pro Phe Lys Glu Gln Ser Phe Val Tyr Lys Lys Asp Gly Asn
     30                  35                  40 ttc ctt aag ctc cca gat aca gac tgc agg cag aca cct ccc ttc ctc       255
Phe Leu Lys Leu Pro Asp Thr Asp Cys Arg Gln Thr Pro Pro Phe Leu
 45                  50                  55 gtc ctg ctg gtg acc tca tcc cac aaa cag ttg gct gag cgc atg gcc       303
Val Leu Leu Val Thr Ser Ser His Lys Gln Leu Ala Glu Arg Met Ala
 60                  65                  70                  75 atc cgg cag acg tgg ggg aaa gag agg acg gtg aag gga aag cag ctg       351
Ile Arg Gln Thr Trp Gly Lys Glu Arg Thr Val Lys Gly Lys Gln Leu
                 80                  85                  90 aag aca ttc ttc ctc ctg ggg acc acc agc agt gca gcg gaa aca aaa       399
Lys Thr Phe Phe Leu Leu Gly Thr Thr Ser Ser Ala Ala Glu Thr Lys
             95                 100                 105 gag gtg gac cag gag agc cag cga cac ggg gac att atc cag aag gat       447
Glu Val Asp Gln Glu Ser Gln Arg His Gly Asp Ile Ile Gln Lys Asp
         110                 115                 120 ttc cta gac gtc tat tac aat ctg acc ctg aag acc atg atg ggc ata       495
Phe Leu Asp Val Tyr Tyr Asn Leu Thr Leu Lys Thr Met Met Gly Ile
     125                 130                 135 gaa tgg gtc cat cgc ttt tgt cct cag gcg gcg ttt gtg atg aaa aca       543
Glu Trp Val His Arg Phe Cys Pro Gln Ala Ala Phe Val Met Lys Thr
 140                 145                 150                 155 gac tca gac atg ttc atc aat gtt gac tat ctg act gaa ctg ctt ctg       591
```

-continued

```
Asp Ser Asp Met Phe Ile Asn Val Asp Tyr Leu Thr Glu Leu Leu Leu
            160                 165                 170 aag aaa aac aga aca acc agg ttt ttc act ggc ttc ttg aaa ctc aat       639
Lys Lys Asn Arg Thr Thr Arg Phe Phe Thr Gly Phe Leu Lys Leu Asn
                175                 180                 185 gag ttt ccc atc agg cag cca ttc agc aag tgg ttt gtc agt aaa tct       687
Glu Phe Pro Ile Arg Gln Pro Phe Ser Lys Trp Phe Val Ser Lys Ser
        190                 195                 200 gaa tat ccg tgg gac agg tac cca cca ttc tgc tcc ggc acc ggc tac       735
Glu Tyr Pro Trp Asp Arg Tyr Pro Pro Phe Cys Ser Gly Thr Gly Tyr
    205                 210                 215 gtg ttt tct ggc gac gtg gcg agt cag gtg tac aat gtc tcc aag agc       783
Val Phe Ser Gly Asp Val Ala Ser Gln Val Tyr Asn Val Ser Lys Ser
220                 225                 230                 235 gtc cca tac att aaa ctg gaa gac gtg ttt gtg ggg ctc tgc ctc gaa       831
Val Pro Tyr Ile Lys Leu Glu Asp Val Phe Val Gly Leu Cys Leu Glu
                240                 245                 250 agg ctg aac atc aga ttg gag gag ctc cac tcc cag ccg acc ttt ttt       879
Arg Leu Asn Ile Arg Leu Glu Glu Leu His Ser Gln Pro Thr Phe Phe
                255                 260                 265 cca ggg ggc tta cgc ttc tcc gta tgc ctc ttc agg agg atc gtg gcc       927
Pro Gly Gly Leu Arg Phe Ser Val Cys Leu Phe Arg Arg Ile Val Ala
        270                 275                 280 tgc cac ttc atc aag cct cgg act ctc ttg gac tac tgg cag gct cta       975
Cys His Phe Ile Lys Pro Arg Thr Leu Leu Asp Tyr Trp Gln Ala Leu
285                 290                 295 gag aat tcc cgg ggg gaa gat tgt ccg cct gtc tga                      1011
Glu Asn Ser Arg Gly Glu Asp Cys Pro Pro Val
300                 305                 310

<210> SEQ ID NO 9
<211> LENGTH: 310
<212> TYPE: PRT
<213> ORGANISM: Homo sapiens

<400> SEQUENCE: 9

Met Ala Phe Pro Lys Met Arg Leu Met Tyr Ile Cys Leu Leu Val Leu
1               5                   10                  15

Gly Ala Leu Cys Leu Tyr Phe Ser Met Tyr Ser Leu Asn Pro Phe Lys
            20                  25                  30

Glu Gln Ser Phe Val Tyr Lys Lys Asp Gly Asn Phe Leu Lys Leu Pro
        35                  40                  45

Asp Thr Asp Cys Arg Gln Thr Pro Pro Phe Leu Val Leu Leu Val Thr
    50                  55                  60

Ser Ser His Lys Gln Leu Ala Glu Arg Met Ala Ile Arg Gln Thr Trp
65                  70                  75                  80

Gly Lys Glu Arg Thr Val Lys Gly Lys Gln Leu Lys Thr Phe Phe Leu
                85                  90                  95

Leu Gly Thr Thr Ser Ser Ala Ala Glu Thr Lys Glu Val Asp Gln Glu
            100                 105                 110

Ser Gln Arg His Gly Asp Ile Ile Gln Lys Asp Phe Leu Asp Val Tyr
        115                 120                 125

Tyr Asn Leu Thr Leu Lys Thr Met Gly Ile Glu Trp Val His Arg
    130                 135                 140

Phe Cys Pro Gln Ala Ala Phe Val Met Lys Thr Asp Ser Asp Met Phe
145                 150                 155                 160

Ile Asn Val Asp Tyr Leu Thr Glu Leu Leu Leu Lys Lys Asn Arg Thr
                165                 170                 175
```

```
Thr Arg Phe Phe Thr Gly Phe Leu Lys Leu Asn Glu Phe Pro Ile Arg
            180                 185                 190

Gln Pro Phe Ser Lys Trp Phe Val Ser Lys Ser Glu Tyr Pro Trp Asp
        195                 200                 205

Arg Tyr Pro Pro Phe Cys Ser Gly Thr Gly Tyr Val Phe Ser Gly Asp
    210                 215                 220

Val Ala Ser Gln Val Tyr Asn Val Ser Lys Ser Val Pro Tyr Ile Lys
225                 230                 235                 240

Leu Glu Asp Val Phe Val Gly Leu Cys Leu Glu Arg Leu Asn Ile Arg
                245                 250                 255

Leu Glu Glu Leu His Ser Gln Pro Thr Phe Pro Gly Gly Leu Arg
            260                 265                 270

Phe Ser Val Cys Leu Phe Arg Ile Val Ala Cys His Phe Ile Lys
        275                 280                 285

Pro Arg Thr Leu Leu Asp Tyr Trp Gln Ala Leu Glu Asn Ser Arg Gly
    290                 295                 300

Glu Asp Cys Pro Pro Val
305                 310

<210> SEQ ID NO 10
<211> LENGTH: 422
<212> TYPE: PRT
<213> ORGANISM: Homo sapiens

<400> SEQUENCE: 10

Met Leu Gln Trp Arg Arg His Cys Cys Phe Ala Lys Met Thr Trp
  1               5                  10                  15

Asn Ala Lys Arg Ser Leu Phe Arg Thr His Leu Ile Gly Val Leu Ser
             20                  25                  30

Leu Val Phe Leu Phe Ala Met Phe Leu Phe Asn His His Asp Trp
         35                  40                  45

Leu Pro Gly Arg Ala Gly Phe Lys Glu Asn Pro Val Thr Tyr Thr Phe
     50                  55                  60

Arg Gly Phe Arg Ser Thr Lys Ser Glu Thr Asn His Ser Ser Leu Arg
 65                  70                  75                  80

Asn Ile Trp Lys Glu Thr Val Pro Gln Thr Leu Arg Pro Gln Thr Ala
                 85                  90                  95

Thr Asn Ser Asn Asn Thr Asp Leu Ser Pro Gln Gly Val Thr Gly Leu
            100                 105                 110

Glu Asn Thr Leu Ser Ala Asn Gly Ser Ile Tyr Asn Glu Lys Gly Thr
        115                 120                 125

Gly His Pro Asn Ser Tyr His Phe Lys Tyr Ile Ile Asn Glu Pro Glu
    130                 135                 140

Lys Cys Gln Glu Lys Ser Pro Phe Leu Ile Leu Leu Ile Ala Ala Glu
145                 150                 155                 160

Pro Gly Gln Ile Glu Ala Arg Arg Ala Ile Arg Gln Thr Trp Gly Asn
                165                 170                 175

Glu Ser Leu Ala Pro Gly Ile Gln Ile Thr Arg Ile Phe Leu Leu Gly
            180                 185                 190

Leu Ser Ile Lys Leu Asn Gly Tyr Leu Gln Arg Ala Ile Leu Glu Glu
        195                 200                 205

Ser Arg Gln Tyr His Asp Ile Ile Gln Gln Glu Tyr Leu Asp Thr Tyr
    210                 215                 220

Tyr Asn Leu Thr Ile Lys Thr Leu Met Gly Met Asn Trp Val Ala Thr
```

```
                225                 230                 235                 240
Tyr Cys Pro His Ile Pro Tyr Val Met Lys Thr Asp Ser Asp Met Phe
            245                 250                 255
Val Asn Thr Glu Tyr Leu Ile Asn Lys Leu Leu Lys Pro Asp Leu Pro
            260                 265                 270
Pro Arg His Asn Tyr Phe Thr Gly Tyr Leu Met Arg Gly Tyr Ala Pro
            275                 280                 285
Asn Arg Asn Lys Asp Ser Lys Trp Tyr Met Pro Pro Asp Leu Tyr Pro
            290                 295                 300
Ser Glu Arg Tyr Pro Val Phe Cys Ser Gly Thr Gly Tyr Val Phe Ser
305                 310                 315                 320
Gly Asp Leu Ala Glu Lys Ile Phe Lys Val Ser Leu Gly Ile Arg Arg
            325                 330                 335
Leu His Leu Glu Asp Val Tyr Val Gly Ile Cys Leu Ala Lys Leu Arg
            340                 345                 350
Ile Asp Pro Val Pro Pro Asn Glu Phe Val Phe Asn His Trp Arg
            355                 360                 365
Val Ser Tyr Ser Ser Cys Lys Tyr Ser His Leu Ile Thr Ser His Gln
            370                 375                 380
Phe Gln Pro Ser Glu Leu Ile Lys Tyr Trp Asn His Leu Gln Gln Asn
385                 390                 395                 400
Lys His Asn Ala Cys Ala Asn Ala Ala Lys Glu Lys Ala Gly Arg Tyr
            405                 410                 415
Arg His Arg Lys Leu His
            420

<210> SEQ ID NO 11
<211> LENGTH: 326
<212> TYPE: PRT
<213> ORGANISM: Homo sapiens

<400> SEQUENCE: 11

Met Ala Ser Lys Val Ser Cys Leu Tyr Val Leu Thr Val Val Cys Trp
1               5                   10                  15
Ala Ser Ala Leu Trp Tyr Leu Ser Ile Thr Arg Pro Thr Ser Ser Tyr
            20                  25                  30
Thr Gly Ser Lys Pro Phe Ser His Leu Thr Val Ala Arg Lys Asn Phe
        35                  40                  45
Thr Phe Gly Asn Ile Arg Thr Arg Pro Ile Asn Pro His Ser Phe Glu
    50                  55                  60
Phe Leu Ile Asn Glu Pro Asn Lys Cys Glu Lys Asn Ile Pro Phe Leu
65                  70                  75                  80
Val Ile Leu Ile Ser Thr His Lys Glu Phe Asp Ala Arg Gln Ala
            85                  90                  95
Ile Arg Glu Thr Trp Gly Asp Glu Asn Asn Phe Lys Gly Ile Lys Ile
            100                 105                 110
Ala Thr Leu Phe Leu Leu Gly Lys Asn Ala Asp Pro Val Leu Asn Gln
        115                 120                 125
Met Val Glu Gln Glu Ser Gln Ile Phe His Asp Ile Val Glu Asp
    130                 135                 140
Phe Ile Asp Ser Tyr His Asn Leu Thr Leu Lys Thr Leu Met Gly Met
145                 150                 155                 160
Arg Trp Val Ala Thr Phe Cys Ser Lys Ala Lys Tyr Val Met Lys Thr
            165                 170                 175
```

-continued

Asp Ser Asp Ile Phe Val Asn Met Asp Asn Leu Ile Tyr Lys Leu Leu
            180                 185                 190

Lys Pro Ser Thr Lys Pro Arg Arg Tyr Phe Thr Gly Tyr Val Ile
        195                 200                 205

Asn Gly Gly Pro Ile Arg Asp Val Arg Ser Lys Trp Tyr Met Pro Arg
    210                 215                 220

Asp Leu Tyr Pro Asp Ser Asn Tyr Pro Pro Phe Cys Ser Gly Thr Gly
225                 230                 235                 240

Tyr Ile Phe Ser Ala Asp Val Ala Glu Leu Ile Tyr Lys Thr Ser Leu
                245                 250                 255

His Thr Arg Leu Leu His Leu Glu Asp Val Tyr Val Gly Leu Cys Leu
            260                 265                 270

Arg Lys Leu Gly Ile His Pro Phe Gln Asn Ser Gly Phe Asn His Trp
        275                 280                 285

Lys Met Ala Tyr Ser Leu Cys Arg Tyr Arg Arg Val Ile Thr Val His
    290                 295                 300

Gln Ile Ser Pro Glu Glu Met His Arg Ile Trp Asn Asp Met Ser Ser
305                 310                 315                 320

Lys Lys His Leu Arg Cys
                325

<210> SEQ ID NO 12
<211> LENGTH: 331
<212> TYPE: PRT
<213> ORGANISM: Homo sapiens

<400> SEQUENCE: 12

Met Ala Ser Ala Leu Trp Thr Val Leu Pro Ser Arg Met Ser Leu Arg
1               5                   10                  15

Ser Leu Lys Trp Ser Leu Leu Leu Ser Leu Leu Ser Phe Phe Val
                20                  25                  30

Met Trp Tyr Leu Ser Leu Pro His Tyr Asn Val Ile Glu Arg Val Asn
            35                  40                  45

Trp Met Tyr Phe Tyr Glu Tyr Glu Pro Ile Tyr Arg Gln Asp Phe His
        50                  55                  60

Phe Thr Leu Arg Glu His Ser Asn Cys Ser His Gln Asn Pro Phe Leu
65                  70                  75                  80

Val Ile Leu Val Thr Ser His Pro Ser Asp Val Lys Ala Arg Gln Ala
                85                  90                  95

Ile Arg Val Thr Trp Gly Glu Lys Lys Ser Trp Gly Tyr Glu Val
            100                 105                 110

Leu Thr Phe Phe Leu Leu Gly Gln Glu Ala Glu Lys Glu Asp Lys Met
        115                 120                 125

Leu Ala Leu Ser Leu Glu Asp Glu His Leu Leu Tyr Gly Asp Ile Ile
    130                 135                 140

Arg Gln Asp Phe Leu Asp Thr Tyr Asn Asn Leu Thr Leu Lys Thr Ile
145                 150                 155                 160

Met Ala Phe Arg Trp Val Thr Glu Phe Cys Pro Asn Ala Lys Tyr Val
                165                 170                 175

Met Lys Thr Asp Thr Asp Val Phe Ile Asn Thr Gly Asn Leu Val Lys
            180                 185                 190

Tyr Leu Leu Asn Leu Asn His Ser Glu Lys Phe Phe Thr Gly Tyr Pro
        195                 200                 205

Leu Ile Asp Asn Tyr Ser Tyr Arg Gly Phe Tyr Gln Lys Thr His Ile
    210                 215                 220

```
Ser Tyr Gln Glu Tyr Pro Phe Lys Val Phe Pro Tyr Cys Ser Gly
225                 230                 235                 240

Leu Gly Tyr Ile Met Ser Arg Asp Leu Val Pro Arg Ile Tyr Glu Met
            245                 250                 255

Met Gly His Val Lys Pro Ile Lys Phe Glu Asp Val Tyr Val Gly Ile
        260                 265                 270

Cys Leu Asn Leu Lys Val Asn Ile His Ile Pro Glu Asp Thr Asn
    275                 280                 285

Leu Phe Phe Leu Tyr Arg Ile His Leu Asp Val Cys Gln Leu Arg Arg
290                 295                 300

Val Ile Ala Ala His Gly Phe Ser Ser Lys Glu Ile Ile Thr Phe Trp
305                 310                 315                 320

Gln Val Met Leu Arg Asn Thr Thr Cys His Tyr
                325                 330
```

```
<210> SEQ ID NO 13
<211> LENGTH: 378
<212> TYPE: PRT
<213> ORGANISM: Homo sapiens

<400> SEQUENCE: 13

Met Gln Leu Arg Leu Phe Arg Arg Leu Leu Ala Ala Leu Leu Leu
1               5                   10                  15

Val Ile Val Trp Thr Leu Phe Gly Pro Ser Gly Leu Gly Glu Glu Leu
                20                  25                  30

Leu Ser Leu Ser Leu Ala Ser Leu Pro Ala Pro Ala Ser Pro Gly
            35                  40                  45

Pro Pro Leu Ala Leu Pro Arg Leu Leu Ile Pro Asn Gln Glu Ala Cys
    50                  55                  60

Ser Gly Pro Gly Ala Pro Pro Phe Leu Leu Ile Leu Val Cys Thr Ala
65                  70                  75                  80

Pro Glu Asn Leu Asn Gln Arg Asn Ala Ile Arg Ala Ser Trp Gly Gly
                85                  90                  95

Leu Arg Glu Ala Arg Gly Leu Arg Val Gln Thr Leu Phe Leu Leu Gly
            100                 105                 110

Glu Pro Asn Ala Gln His Pro Val Trp Gly Ser Gln Gly Ser Asp Leu
        115                 120                 125

Ala Ser Glu Ser Ala Ala Gln Gly Asp Ile Leu Gln Ala Ala Phe Gln
    130                 135                 140

Asp Ser Tyr Arg Asn Leu Thr Leu Lys Thr Leu Ser Gly Leu Asn Trp
145                 150                 155                 160

Ala Glu Lys His Cys Pro Met Ala Arg Tyr Val Leu Lys Thr Asp Asp
                165                 170                 175

Asp Val Tyr Val Asn Val Pro Glu Leu Val Ser Glu Leu Val Leu Arg
            180                 185                 190

Gly Gly Arg Trp Gly Gln Trp Glu Arg Ser Thr Glu Pro Gln Arg Glu
        195                 200                 205

Ala Glu Gln Glu Gly Gly Gln Val Leu His Ser Glu Glu Val Pro Leu
    210                 215                 220

Leu Tyr Leu Gly Arg Val His Trp Arg Val Asn Pro Ser Arg Thr Pro
225                 230                 235                 240

Gly Gly Arg Gly Arg Val Ser Glu Glu Gln Trp Pro His Thr Trp Gly
                245                 250                 255

Pro Phe Pro Pro Tyr Ala Ser Gly Thr Gly Tyr Val Leu Ser Ala Ser
```

-continued

```
                     260                 265                 270
Ala Val Gln Leu Ile Leu Lys Val Ala Ser Arg Ala Pro Leu Leu Pro
            275                 280                 285

Leu Glu Asp Val Phe Val Gly Val Ser Ala Arg Arg Gly Gly Leu Ala
            290                 295                 300

Pro Thr Gln Cys Val Lys Leu Ala Gly Ala Thr His Tyr Pro Leu Asp
305                 310                 315                 320

Arg Cys Cys Tyr Gly Lys Phe Leu Leu Thr Ser His Arg Leu Asp Pro
                325                 330                 335

Trp Lys Met Gln Glu Ala Trp Lys Leu Val Gly Gly Ser Asp Gly Glu
                340                 345                 350

Arg Thr Ala Pro Phe Cys Ser Trp Phe Gln Gly Val Leu Gly Ile Leu
            355                 360                 365

Arg Cys Arg Ala Ile Ala Trp Leu Gln Ser
    370                 375

<210> SEQ ID NO 14
<211> LENGTH: 30
<212> TYPE: DNA
<213> ORGANISM: Homo sapiens

<400> SEQUENCE: 14
cggggtaccg gaaacgatga aatatacaag                                      30

<210> SEQ ID NO 15
<211> LENGTH: 40
<212> TYPE: DNA
<213> ORGANISM: Homo sapiens

<400> SEQUENCE: 15
ggcggatcca ggcagatcac agccaagaga acccaaaacg                           40

<210> SEQ ID NO 16
<211> LENGTH: 40
<212> TYPE: DNA
<213> ORGANISM: Homo sapiens

<400> SEQUENCE: 16
gcggatccca ggcagatcac agccaagaga acccaaaacg                           40

<210> SEQ ID NO 17
<211> LENGTH: 41
<212> TYPE: DNA
<213> ORGANISM: Homo sapiens

<400> SEQUENCE: 17
gcggatcccc aggcagatca cagccaagag aacccaaaac g                         41
```